US006342593B1

(12) United States Patent
Plowman et al.

(10) Patent No.: US 6,342,593 B1
(45) Date of Patent: Jan. 29, 2002

(54) DIAGNOSIS AND TREATMENT OF ALP RELATED DISORDERS

(75) Inventors: Gregory D. Plowman, San Carlos, CA (US); Elior Peles, Rehovot (IL)

(73) Assignee: Sugen, Inc., South San Francisco, CA (US)

( * ) Notice: Subject to any disclaimer, the term of this patent is extended or adjusted under 35 U.S.C. 154(b) by 0 days.

(21) Appl. No.: 09/095,443

(22) Filed: Jun. 10, 1998

Related U.S. Application Data

(60) Provisional application No. 60/049,477, filed on Jun. 11, 1997.

(51) Int. Cl.[7] .......................... C07H 21/02; C07H 21/04
(52) U.S. Cl. .................... 536/23.1; 536/23.5; 536/24.3; 536/24.31; 536/24.33; 530/350
(58) Field of Search ....................... 530/350; 536/23.1, 536/23.5, 24.3, 24.31, 24.33

(56) References Cited

U.S. PATENT DOCUMENTS

| | | | |
|---|---|---|---|
| 4,343,940 A | 8/1982 | Kreighbaum et al. | 544/283 |
| 4,376,110 A | 3/1983 | David et al. | 436/513 |
| 4,447,608 A | 5/1984 | Jones et al. | 544/287 |
| 4,757,072 A | 7/1988 | Kabbe et al. | 514/257 |
| 4,945,050 A | 7/1990 | Sanford et al. | 435/172.1 |
| 5,217,999 A | 6/1993 | Levitzki et al. | 514/613 |
| 5,283,173 A | 2/1994 | Fields et al. | 435/6 |
| 5,302,606 A | 4/1994 | Spada et al. | 514/357 |
| 5,316,553 A | 5/1994 | Kaul et al. | 8/639 |
| 5,330,992 A | 7/1994 | Eissenstat et al. | 514/312 |
| 5,602,171 A | 2/1997 | Tang et al. | 514/455 |
| 5,610,173 A | 3/1997 | Schwartz et al. | 514/378 |

FOREIGN PATENT DOCUMENTS

| | | |
|---|---|---|
| EP | 0 520 722 A1 | 12/1992 |
| EP | 0 562 734 A1 | 9/1993 |
| EP | 0 566 226 A1 | 10/1993 |
| WO | 91/15495 | 10/1991 |
| WO | 92/20642 | 11/1992 |
| WO | 92/21660 | 12/1992 |
| WO | 93/09236 | 5/1993 |
| WO | 94/01119 | 1/1994 |
| WO | 94/03427 | 2/1994 |
| WO | 94/14808 | 7/1994 |
| WO | 94/23039 | 10/1994 |
| WO | 96/22976 | 8/1996 |

OTHER PUBLICATIONS

Adams, M., Complementary DNA Sequencing: Expressed Sequence Tags and Human Genome Project, Science, 252, pp. 1651–1656, Jun. 21, 1991.*
Arimura et al., cDNA cloning of new protein tyrosine phosphatases in the human colon, Tumor Biology 13(3) pp. 180–186, 1992.*
Gu et al., Proc. Natl. Acad. Sci, USA 89(7), pp. 2980–2984, 1992.*
Marra, M. et al, Accession AA637137, 1996.*
Marra, M. et al., Accession AA140178, 1996.*
Marra, M. et al., Accession AA139256, 1996.*
Hillier, L. et al., Acession R88521, 1995.*
Hillier, L. et al., Accession R88521, 1995.*
Hillier, L. et al., Accession H39019, 1995.*
Adams, M et al., Accession M62236, 1991.*
Arimura et al., Accession S39392, 1992.*
Gu et al., Accession M83738, 1992.*
Sambrook et al., Molecular Cloning, A Laboratory Manual, vol. 3, pp. 17.3–17.9, 1989.*
Ausubel et al., Current Protocols in Molecular biology, vol. 2, pp. 16.6.1–16.6.12 and 16.7.1–16.7.8, Jun. 21, 1991.*
Abe et al., "Molecular Characterization of a Novel Metabotropic Glutamate Receptor mGluR5 Coupled to Inositol Pohosphate/$Ca^{2+}$ Signal," *J. Biol. Chem.* 267(19):13361–13368 (1992).
Allen et al., "Modulation of CD4 by suramin," *Clin. Exp. Immunol.* 91:141–146 (1991).
Altschul et al., "Basic Local Alignment Search Tool," *J. Mol. Biol.* 215:403–410 (1990).
Anafi et al., "Tyrphostin–Induced Inhibition of $p210^{bcr-abl}$ Tyrosine Kinase Activity Induces K562 to Differentiate," *Blood* 82:3524–3529 (1993).
Baker et al., "Induction of acetylcholine receptor clustering by native polystyrene beads," *Journal of Cell Science* 102:543–555 (1992).
Barker et al., "In vitro activity of non–glutamate containing quinazoline–based thymidylate synthase inhibitors," *Proceedings of the American Association for Cancer Research* 32:327 at abstract No. 1939 (1991).
Bayer et al., "The Avidin—Biotin Complex in Affinity Cytochemistry," *Meth. Enzym.* 62:308 (1979).
Benoist and Chambon, "In vivo sequence requirements of the SV40 early promoter region," *Nature* 290:304–310 (1981).
Bertino, "Toward Improved Selectivity in Cancer Chemotherapy: The Richard and Hinda Rosenthal Foundation Award Lecture," *Cancer Research* 39:293–304 (1979).
Bilder et al., "Tyrphostins inhibit PDGF–induced DNA synthesis and associated early events in smooth muscle cells," *Am. J. Physiol.* 260 (Cell Physiol.29): C721–C730 (1991).
Bollon et al., "DNA Transformation Efficency of Various Bacterial and Yeast Host–Vector Systems,"*J. Clin. Hematol. Oncoll.* 10:39–48 (1980).

(List continued on next page.)

Primary Examiner—Anthony C. Caputa
Assistant Examiner—Jennifer Hunt
(74) *Attorney, Agent, or Firm*—Foley & Lardner

(57) ABSTRACT

The present invention relates to Alp polypeptides, nucleic acids encoding such polypeptides, cells, tissues and animals containing such nucleic acids, antibodies to such polypeptides, assays utilizing such polypeptides, and methods relating to all of the foregoing. Methods for treatment, diagnosis, and screening are provided for Alp related diseases or conditions characterized by an abnormal interaction between an Alp polypeptide and an Alp binding partner.

9 Claims, No Drawings

OTHER PUBLICATIONS

Botstein et al., "Making Mutations In Vitro and Putting Them Back Into Yeast," *Miami Wntr. Symp.* 19:265–274 (1982).

Brinster et al., "Factors Affecting the Efficiency of Introducing Foreign DNA into Mice by Microinjecting Eggs," *Proc. Natl. Acad. Sci. USA* 82:4438–4442 (1985).

Broach, "The Yeast Plasmid $2\mu$ Circle," *Cell* 28:203–204 (1982).

Broach, In: *The Molecular Biology of the Yeast Saccharomyces: Life Cycle and Inheritance*, Cold Spring Harbor Laboratory, Cold Spring Harbor, NY, pp. 445–470.

Brunton et al., "Anti–tumor activity of novel tryphostins in breast cancer cells," *Proceedings of the American Association for Cancer Research* 33:558 at abstract No. 3335 (1992).

Bryckaert et al., "Inhibition of Platelet–Derived Growth Factor–Induced Mitogenesis and Tyrosine Kinase Activity in Cultured Bone Marrow Fibroblasts by Tyrphostins," *Exp. Cell Research* 199:255–261 (1992).

Bullock et al., *Techniques in Immunocytochemistry*, Academic Press, Orlando, FL vol. 1 (1982), vol. 2 (1983), vol. 3 (1985) pp. xi–xii(vol. 1), ix–x (vol. 2), v–vi (vol. 3) only.

Burke et al., "Arylamides of Hydroxylated Isoquinolines as Protein–Tyrosine Kinase Inhibitors," *Bioorganic & Medical Chemistry Letters* 2(12):1771–1774 (1992).

Burke et al., "Bicyclic Compounds as Ring–Constrained Inhibitors of Protein–Tyrosine Kinase p56$^{lck\ 1}$," *Journal of Medicinal Chemistry* 36(4):425–432 (1993).

Campbell, *Monoclonal Antibody Technology: Laboratory Tchniques in Biochemistry and Molecular Biology*, Elsevier Science Publishers, Amsterdam, The Netherlands, (1984) pp. ix–ixv only.

Capecchi MR, "High Efficency by Direct Microinjection of DNA into Cultured Mammalian Cells," *Cell* 22:479–88 (1980).

Capecchi, "Altering the Genome by Homologous Recombination," *Science* 244:1288–1292 (1989).

Cenatiempo, "Prokaryotic Gene Expression In Vitro: Transcription—Translation Coupled Systems," *Biochimie* 68:505–516 (1986).

Chard, "An Introduction to Radioimmunoassay and Related Techniques," Elsevier Science Publishers, Amsterdam, The Netherlands (1986) vii–xiii only.

Chater et al., In: *Sixth International Symposium on Actinomycetales Biology*, Akademiai Kaido, Budapest, Hungary (1986) pp. 45–54.

Chen and Okayama, "High–Effiency Transformation of Mammalian Cells by Plasmid DNA," *Molecular and Cellular Biology* 7(8):2745–2752 (1987).

Chomczynski and Sacchi, "Single–Step Method of RNA Isolation by Acid Guanidinium Thiocyanate–Phenol–Chloroform Extraction," *Analytical Biochemistry* 162:156–159 (1987).

Chu G., et al., "Electroporation for the Efficient Transfection of Mammalian Cells with DNA," *Nucleic Acids Res.,* 15:1311–26 (1987).

Curtin et al., "Inhibition of the growth of human hepatocellular carcinoma in vitro and in athymic mice by a quinazoline inhibitor of thymidylate synthase, CB3717," *Br. J. Cancer* 53:361–368 (1986).

Dolle et al., "5,7–Dimethoxy–3–(4–pyridinyl)quinoline is a Potent and Selective Inhibitor of Human Vascular—Type Platelet–Derived Growth Factor Receptor Tyrosine Kinase," *J. Med. Chem.* 37:2627–2629 (1994).

Dong et al., "Activation of tumoricidal properties in macrophages by lipopolysaccharide requires protein–tyrosine kinase activity," *Journal of Leukocyte Biology* 53:53–60 (1993).

Dong et al., "Protein Tyrosine Kinase Inhibitors Decrease Induction of Nitric Oxide Synthase Activity in Lipopolysaccharide–Resposinve and Lipopolysaccharide–Nonresponsive Murine Macrophages," *The Journal of Immunology* 151(5):2717–2724 (1993).

Engvall et al., "Enzyme–Liked Immunosorbent Assay, Elisa," *Immunot* 109:129 (1972).

Felgner and Ringold, "Cationic liposome–mediated transfection," *Nature* 337:387–388 (1989).

Felgner et al., "Lipofection: A Highly Efficient, Lipid–mediated DNA–transfection Procedure," *Proc. Natl. Acad. Sci. USA* 84:7413–7147 (1987).

Fernandes et al., "Biochemical and Antitumor Effects of 5,8–Dideazaisopteroylglutamate, a Unique Quinazoline Inhibitor of Thymidylate Synthase," *Cancer Research* 43:1117–1123.

Ferris et al., "Synthesis of Quinazoline Nucleosides from Ribose and Anthranilonitrile. Application of Phase–Transfer Catalysis in Nucleoside Synthesis," *J. Org. Chem.* 44(2):173–178 (1979).

Fingl and Woodbury, "Chapter 1—General Principles," in *The Pharmacological Basis of Therapeutics* 5th edition, Goodman and Gilman editors, MacMillan Publishing Co., Inc., New York, pp. 1–46 (1975).

Fry et al., "A Specific Inhibitor of the Epidermal Growth Factor Receptor Tyrosine Kinase," *Science* 265:1093–1095 (1994).

Gazit et al., "Tyrphostins 1. Synthesis and Biological Activity of Protein Tyrosine Kinase Inhibitors," *J. Med. Chem.* 32:2344–2352 (1989).

Gazit et al., "Tyrphostins. 3. Structure–Activity Relationship Studies of a –Substituted Benzylidenemalononitrile 5–S–Aryltyrphostins," *J. Med. Chem.* 36:3556–3564 (1993).

Gerard, "cDNA Synthesis by Cloned Moloney Murine Leukemia Virus Reverse Transcriptase Lacking Rnase H Activity," *Focus* 11 (4):66–69.

Gilman et al., "Isolation of Sigma–28–Specific Promoters from *Bacillus Subtilis* DNA," *Gene* 32:11–20 (1984).

Glick, "Factors Affecting the Expression of Foreign Proteins in *Escherichia coli,*" *J. Ind. Microbiot.* 1:277–282 (1987).

Goding, "Conjugation of Antibodies with Fluorochromes: Modifications to the Standard Methods," *J. Immunological Methods* 13:215–226 (1976).

Gold et al., "Translational Initiation in Prokaryotes," *Ann. Rev. Microbiol.* 35:365–404 (1981).

Gottesman, "Bacterial Regulation: Global Regulatory Networks," *Ann. Rev. Genet.* 18:415–441 (1984).

Gryczan, In: The Molecular Biology of the Bacilli, Acadmic Press, Inc., NY (1982).

Hamer et al., "Regulation In Vivo of a Cloned Mammalian Gene: Cadmium Induces the Transcription of a Mouse Metallothionein gene in SV$) Vectors," *J. Mol. Appl. Gen.* 1:273–288 (1982).

Hammer et al., "Spontaneous Inflammatory Disease in Transgenic Rats Expressing HLA–B27 and Human $_2$m: An Animal Model of HLA–B27–Associated Human Disorders," *Cell* 63:1099–1112 (1990).

Hanks and Hunter, "The Eukaryotic Protine Kinase Superfamily: Kinase (Catalytic) Domain Structure and Classification," *FASEB J* 9:576–595 (1995).

Haslam et al., "Pleckstrin Domain Homology," *Nature* 363:309 (1993).

Houdebine and Chourrout, "Transgenesis in Fish," *Experientia* 47:891–897 (1991).

Hurby et al., in *Synthetic Peptides: A User's Guide,* edited by Grant, Washington University School of Medicine, W.H. Freeman and Company, New York, pp. 289–307 (1992).

Innis et al., *PCR Protocols: A Guide to Methods and Applications,* edited by Michael A. Innis et al., Academic Press, San Diego (1990) (Table of Contents Only).

Izaki, *Jpn. J. Bacteriol.* 33:729–742 (1978).

Jackman, "ICI D1694, a Quinazoline Antifolate Thymidylate Synthase Inhibitor That Is a Potent Inhibitor of L1210 Tumor Cell Growth in Vitro and in Vivo: A New Agent for Clinical Study," *Cancer Research* 51:5579–5586 (1991).

Jakoby et al., *Meth. Enzym.* 34:Index (1974).

Jasny, "Insect Viruses Invade Biotechnology," *Science* 238:1653 (1987).

John et al., "Plasmids as Epidemiologic Markers in Nosocomial Gram–Negative Bacilli: Experience at a University and Review of the Literature," *Rev. Infect. Dis.* 8:693–704 (1986).

Johnston and Hopper, "Isolation of the yeast regulatory gene GAL4 and analysis of its dosage effects on the galactose/melibiose regulon," *Proc. Natl. Acad. Sci. USA* 79:6971–6975 (1982).

Jones et al., "Quinazoline Antifolates Inhibiting Thymidylate Synthase: Variation of the Amino Acid," *J. Med. Chem.* 29:1114–1118 (1986).

Joyner et al., "Production of a mutation in mouse En–2 gene by homologous recombination in embryonic stem cells," *Nature* 338:153–156 (1989).

Kasprzak et al., "Location of a Contact Site Between Actin and Myosin in the Three–Dimensional Structure of the Acto–S1 Complex," *Biochemistry* 28:9230–8 (1989).

Kaur, "Tyrphostin induced growth inhibition: correlation with effect on p210$^{bcr-abl}$ autokinase activity in K562 chronic myelogenous leukemia," *Anti–Cancer Drugs* 5:213–222 (1994).

Kendall et al., "Plasmid Transfer in Streptomyces Lividans: Identification of a kil–kor System Associated with the Transfer Region of pIJ101," *J. Bacteriol.* 169:4177–4183 (1987).

King et al.,"Site–specific dephosphorylation and deactivation of the human insulin receptor tyrosine kinase by particulate and soluble phosphotyrosyl protein phosphatases," *Biochem. J.* 275:413–418 (1991).

Köhler (Kohler) and Milstein, "Continuous cultures of fused cells secreting antibody of predefined specificity," *Nature* 256:495–497 (1975).

Krueger et al., "A Human Transmembrane Protein–Tyrosine–Phosphatase, PTPξ, is Expressed in Brain and has an N–Terminal Receptor Domain Homologous to Carbonic Anhydrases," *Proc. Natl. Acad. Sci. USA* 89:7417–7421 (1992).

Kuo et al., "Effects of signalling transduction modulators on the transformed phenotypes in v–H–ras–transformed NIH 3T3 cells," *Cancer Letters* 74:197–202 (1993).

Lee and Skibo, "Active–Site–Directed Reductive Alkylation of Xanthine Oxidase by Imidazo[4,5–g]guinazoline–4,9–diones Functionalized with a Leaving Group," *Biochemistry* 26:7355–7362 (1987).

Lemus et al., "Studies of Extended Quinone Methides. Synthesis and Physical Studies of Purine–like Monofunctional and Bifunctional Imidazo[4,5–g]quinazoline Reductive Alkylating Agents," *J. Org. Chem.* 54:3611–3618 (1989).

Levitzki, "Tyrphostins: tyrosine kinase blockers as novel antiproliferative agents and dissectors of signal transcution," *FASEB J.* 6:3275–3282 (1992).

Ley and Seng, "Synthesis Using Benzofuroxan," *Synthesis* 1975:415–422 (1975).

Lutz et al., "The Distribution of Two hnRNP–Associated Proteins Defined by a Monoclonal Antibody Is Altered in Heat–Shocked HeLa Cells," *Experimental Cell Research* 175:109–124 (1988).

Lyall et al., "Tyrphostins Inhibit Epidermal Growth Factor (EGF)–Receptor Tyrosine Kinase Activity in Living Cells and EGF–stimulated Cell Proliferation," *J. Biol. Chem.* 264:14503–14509 (1989).

Maguire et al., "A new series of PDGF Receptor Tyrosine Kinase Inhibitors: 3–Substituted Quinoline Derivatives," *J. Med. Chem.* 37:2129–2137 (1994).

Maniatis, In: *Cell Biology: A Comprehensive Treatise,* vol. 3 Gene Sequences Expression, Academic Press, NY, pp. 563–608 (1980).

Maxwell et al., "$^{19}$F Nuclear Magnetic Resonance Imaging of Drug Distribution in Vivo: The Disposition of an Antifolate Anticancer Drug in Mice," *Magnetic Resonance in Medicine* 17:189–196 (1991).

Mayer and Baltimore, "Signalling Through SH2 and SH3 Domains," *Trends Cell. Biol.* 3:8 (1993).

Mayer et al., "A novel viral oncogene with structural similarity to phospholipase C," *Nature* 332:272–275 (1988).

McKnight, "Functional Relationships between Transcriptional Control Signals of the Thymidine Kinase Gene of Herpes Simplex Virus," *Cell* 31:355–365 (1982).

Miller et al., In: *Genetic Engineering* (1986) Setlow, J. K., et al., eds., Plenum, vol. 8, pp. 277–297.

Miller, "Human gene therapy comes of age," *Nature* 357:455–460 (1992).

Mini et al., "Cytotoxic Effects of Folate Antagonists against Methotrexate–resistant Human Leukemic Lymphoblast CCRF–CEM Cell Lines," *Cancer Research* 45:325–330 (1985).

Morton and Campbell, "Moelcular 'Velcro*'," *Curr. Biol.* 4(7):614–617 (1994).

Mulligan, "The Basic Science of Gene Therapy," *Science* 260:926–932 (1993).

Nelson, "Detection of Acridinium Esters by Chemiluminescence," *Nonisotopic DNA Probe Techniques,* ed. Larry J. Kricka, (San Diego: Academic Press, Inc.) pp. 275–310 (1992).

Okayama, "A cDNA Cloning Vector That Permits Expression of cDNA Inserts in Mammalian Cells," *Molec. Cell. Bio.* 3:280 (1983).

Pawson and Schlessinger, "SH2 and SH3 domains," *Current Biology* 3(7):434–442 (1993).

Peterson and Barnes, "Genistein and Biochanin A Inhibit the Growth of Human Prostate Cancer Cells but not Epidermal Growth Factor Receptor Tyrosine Autophosphorylation," *The Prostate* 22:335–345 (1993).

Phillips and Castle, "Qunio[1,2–c]quinazolines. I. Synthesis of Quino[1,2–c]quinazolinium Derivatives and the Related Indazolo[2,3–a]quinoline Derivatives as Analogs of the Antitumor Benzo[c]phenanthridine Alkaloids," *J. Heterocyclic Chemistry* 17:1489–1496 (1980).

Pillemer et al., "Insulin Dependence of Murine Lymphoid T–Cell Leukemia," *Int. J. Cancer* 50:80–85 (1992).

Ponting, "Pleckstrin's Repeat Performance: A Novel Domain in G–protein Signaling," *TIBS* 21:245 (1996).

Posner et al., "Kinetics of Inhibition by Tyrphostins of the Tyrosine Kinase Activity of the Epidermal Growth Factor Receptor and Analysis by a New Computer Program," *Molecular Pharmaolcoy* 45:673–683 (1993).

Pursel et al., "Genetic Engineering of Livestock," *Science* 244:1281–1288 (1989).

Redemann et al., "Anti–Oncogenic Activity of Signalling––Defective Epidermal Growth Factor Recpetor Mutants," *Mol. Cell. Biol.* 12:491–498 (1992).

Reece et al., "Pharmacokinetics of Trimetrexate Administered by Five–Day Continuous Infusion to Patients with Advanced Cancer," *Cancer Research* 47:2996–2999 (1987).

Ren et al., "Identification of a Ten–Amino Acid Proline–Rich SH3 Binding Site," *Science* 259:1157–1161 (1993).

Rendu et al., "Inhibition of Platelet Activation by Tyrosine Kinase Inhibitors," *Biochemical Pharmacology* 44(5):881–888 (1992).

Robertson, E.J., ed., *Teratocarcinomas and Embryonic Stem Cells, A Practical Approach*, IRL Press, 1987 pp. vii–xi only.

Rogers et al., "Amino Acid Sequences Common to Rapidly Degraded Proteins: The Pest Hypothesis," *Science* 234:364–368 (1986).

Rubin, "Drosophila Melanogaster as an Experimental Organism," *Science* 240:1453–1459 (1988).

Sadowski et al., A Noncatalytic Domain Conserved among Cytoplasmic Protein–Tyrosine Kinases Modifies the Kinase Function and Transforming Activity of Fujinami Sarcoma Virus P130$^{gag-fps}$, *Molecular and Cellular Biology* 6(12):4396–4408 (1986).

Saito et al., "Molecular Characterization of Protein tyrosine Phosphates," *Cell Growth and Diff.* 2:59–65 (1991).

Sambrook et al., *Molecular Cloning: A Laboratory Manual*, $2^{nd}$ *Edition*, Cold Spring Harbor Press (1989) (Table of Contents for vols. 1,2 and 3).

Sauro and Thomas, "Decreased Sensitivity of Aorta from Hypertensive Rats to Vasorelaxation by Tyrphostin," *Life Sciences* 53:PL371–376 (1993).

Sauro and Thomas, "Tyrphostin Attenuates Platelet–Derived Growth Factor–Induced Contraction in Aortic Smooth Muscle Through Inhibition of Protein Tyrosine Kinase(s)," *The Journal of Pharamacology and Experimental Therapeutics* 267:1119–1125 (1993).

Sculier et al., "Role of an Intensive Care Unit (ICU) in a Medical Oncology Department," *Cancer Immunol. and Immunotherapy* 23:A65 at abstract No. 257 (1986).

Sikora and Grzelakowska–Sztabert, "Quinazoline CB 3717 and CB 3703 Inhibitors of Folate Retention and Metabolism in Ehrlich Ascites Carcinoma Cells and Some Organs of the Host–Mouse," *Cancer Letters* 23:289–295 (1984).

Sikora et al., "Development of an Assay for the Estimation of $N^{10}$–Propargyl–5,8–dideazafolic Acid Polyglutamates in Tumor Cells," *Analytical Biochemistry* 172:344–355 (1988).

Silver et al., "Amino terminus of the yeast GAL4 gene product is sufficient for nuclear localization," *Proc. Natl. Acad. Sci. USA* 81:5951–5955 (1984).

Simons et al., "Gene Transfer into Sheep," *Bio/Technology* 6:179–183 (1988).

St. Groth et al., "Production of Monoclonal Antibodies: Strategy and Tactics," *J. Immunol. Methods* 35:1–21 (1980).

Sternberger et al., "The Unlabeled Antibody Enzyme Method of Immunohistochemistry," *J. Histochem. Cytochem.* 18:315 (1970).

Superti–Furga, et al, "Csk Inhibition of c–Src Activity Requires Both the SH2 and SH3 Domains of Src," *EMBO J.* 12:2625 (1993).

Tijssen, "Practice and Theory of Enzyme Immunoassays," *Laboratory Techniques in Biochemistry and Molecular Biology*, Elsevier Science Publishers, Amsterdam, The Netherlands (1985) pp. ix–xx only.

Ulmanen et al., "Transcription and Translation of Foreign Genes in *Bacillus Subtilis* by the Aid of a Secretion Vector," *J. Bacteriol.* 162:176–182 (1985).

Ward et al., "Construction and Characterisation of a Series of Multi–copy Promoter–probe Plasmid Vectors for Streptomyces Using the Aminoglycoside Phosphotransferase Gene From Tn5 as Indicator," *Mol. Gen. Genet.* 203:468–478 (1986).

Weir et al., *Handbook of Experimental Immunology*, 4th Ed., Blackwell Scientific Publications, Oxford, England, Chapter 10 (1986).

Wolbring et al., "Inhibition of GTP–utilizing Enzymes by Tyrphostins," *J. Biol. Chem.* 269:22470–22472 (1994).

Yang et al., "In vivo and In Vitro Gene Transfer to Mammalian Somatic Cells by Particle Bombardment," *Proc. Natl. Acad. Sci. USA* 87:9568–9572 (1990).

Yoneda et al., "The Antiproliferative Effects of Tyrosine Kinase Inhibitors Tyrphostins on a Human Squamous Cell Carcinoma in Vitro and in Nude Mice," *Cancer Research* 51:4430–4435 (1991).

Hogan et al., "Manipulating the Mouse Enbryo, A Laboratory Manual, Second Edition", pp. ix–xvii (Table of Contents only) ©1994 Cold Spring Harbor Laboratory Press.

* cited by examiner

SEQUENCE LISTING (1) GENERAL INFORMATION:

(iii) NUMBER OF SEQUENCES:       8

(2) INFORMATION FOR SEQ ID NO:    1:

(i) SEQUENCE CHARACTERISTICS:
      (A) LENGTH:         4456 base pairs
      (B) TYPE:           nucleic acid
      (C) STRANDEDNESS:   single
      (D) TOPOLOGY:      linear (xi) SEQUENCE DESCRIPTION: SEQ ID NO:  1:

```
GGCACGAGAG GAGCAGCAGA AGTTCGGGGA GCGGGTTGCA TACTTCCAGA GCGCCCTGGA        60

CAAGCTCAAT GAAGCCATCA AGTTGGCCAA GGGCCAGCCT GACACTGTGC AAGACGCGCT       120

TCGCTTCACT ATGGATGTCA TTGGGGGAAA GTACAATTCT GCCAAGAAGG ACAACGACTT       180
```

-continued

```
CATTTACCAT GAGGCTGTCC CAGCATTGAC ACCCTTCAGC CTGTAAAAGG AGCCCCCTTG    240
GTGAAGCCCT TGCCAGTGAA CCCCACAGAC CCAGCTGTTA CAGGCCCTGA CATCTTTGCC    300
AAACTGGTAC CCATGGCTGC CCACGAGGCC TCGTCACTGT ACAGTGAGGA GAAGGCCAAG    360
CTGCTCCGGG AGATGATGGC CAAGATTGAG GACAAGAATG AGGTCCTGGA CCAGTTCATG    420
GATTCAATGC AGTTGGATCC CGAGACGGTG GACAACCTTG ATGCCTACAG CCACATCCCA    480
CCCCAGCTCA TGGAGAAGTG CGCGGCTCTC AGCGTCCGGC CCGACACTGT CAGGAACCTT    540
GTACAGTCCA TGCAAGTGCT GTCAGGTGTG TTCACGGATG TGGAGGCTTC CCTGAAGGAC    600
ATCAGAGATC TGTTGGAGGA GGATGAGCTG CTAGAGCAGA AGTTTCAGGA GGCGGTGGGC    660
CAGGCAGGGG CCATCTCCAT CACCTCCAAG GCTGAGCTGG CAGAGGTGAG GCGAGAATGG    720
GCCAAGTACA TGGAAGTCCA TGAGAAGGCC TCCTTCACCA ACAGTGAGCT GCACCGTGCC    780
ATGAACCTGC ACGTCGGCAA CCTGCGCCTG CTCAGCGGGC CGCTTGACCA GGTCCGGGCT    840
GCCCTGCCCA CACCGGCCCT CTCCCCAGAG GACAAGGCCG TGCTGCAAAA CCTAAAGCGC    900
ATCCTGGCTA AGGTGCAGGA GATGCGGGAC AGCGCGTGT CCCTGGAGCA GCAGCTGCGT    960
GAGCTTATCC AGAAAGATGA CATCACTGCC TCGCTGGTCA CCACAGACCA CTCAGAGATG   1020
AAGAAGTTGT TCGAGGAGCA GCTGAAAAAG TATGACCAGC TGAAGGTGTA CCTGGAGCAG   1080
AACCTGGCCG CCCAGGACCG TGTCCTCTGT GCACTGACAG AGGCCAACGT GCAGTACGCA   1140
GCCGTGCGGC GGGTACTCAG CGACTTGGAC CAAAAGTGGA ACTCCACGCT GCAGACCCTG   1200
GTGGCCTCGT ATGAAGCCTA TGAGGACCTG ATGAAGAAGT CGCAGGAGGG CAGGGACTTC   1260
TACGCAGATC TGGAGAGCAA GGTGGCTGCT CTGCTGGAGC GCACGCAGTC CACCTGCCAG   1320
GCCCGCGAGG CTGCCCGCCA GCAGCTCCTG GACAGGGAGC TGAAGAAGAA GCCGCCGCCA   1380
CGGCCCACAG CCCCAAAGCC GCTGCTGCCC CGCAGGGAGG AGAGTGAGGC AGTGGAAGCA   1440
GGAGACCCCC CTGAGGAGCT GCGCAGCCTC CCCCCTGACA TGGTGGCTGG CCCACGACTG   1500
CCTGACACCT TCCTGGGAAG TGCCACCCCG CTCCACTTTC CTCCCAGCCC CTTCCCCAGC   1560
TCCACAGGCC CAGGACCCCA CTATCTCTCA GGCCCCTTGC CCCCTGGTAC CTACTCGGGC   1620
CCCACCCAGC TGATACAGCC CAGGGCCCCA GGGCCCCATG CAATGCCCGT AGCACCTGGG   1680
CCTGCCCTCT ACCCAGCCCC TGCCTACACA CCGGAGCTGG GCCTTGTGCC CCGATCCTCC   1740
CCACAGCATG GCGTGGTGAG CAGTCCCTAT GTGGGGGTAG GGCCGGCCCC ACCAGTTGCA   1800
GGTCTCCCCT CGGCCCCACC TCCTCAATTC TCAGGCCCCG AGTTGGCCAT GGCGGTTCGG   1860
CCAGCCACCA CCACAGTAGA TAGCATCCAG GCGCCCATCC CCAGCCACAC AGCCCCACGG   1920
CCAAACCCCA CCCCTGCTCC TCCCCCGCCC TGCTTCCCTG TGCCCCCACC GCAGCCACTG   1980
CCCACGCCTT ACACCTACCC TGCAGGGGCT AAGCAACCCA TCCCAGCACA GCACCACTTC   2040
TCTTCTGGGA TCCCCACAGG TTTTCCAGCC CCAAGGATTG GCCCCAGCC CCAGCCCCAT    2100
CCTCAGCCCC ATCCTTCACA AGCGTTTGGG CCTCAGCCCC CACAGCAGCC CCTTCCACTC   2160
CAGCATCCAC ATCTCTTCCC ACCCCAGGCC CCAGGACTCC TACCCCCACA ATCCCCCTAC   2220
CCCTATGCCC CTCAGCCTGG GGTCCTGGGG CAGCCGCCAC CCCCCCTACA CACCCAGCTC   2280
TACCCAGGTC CCGCTCAAGA CCCTCTGCCA GCCCACTCAG GGGCTCTGCC TTTCCCCAGC   2340
CCTGGGCCCC CTCAGCCTCC CCATCCCCCA CTGGCATATG GTCCTGCCCC TTCTACCAGA   2400
CCCATGGGCC CCCAGGCAGC CCCTCTTACC ATTCGAGGGC CCTCGTCTGC TGGCCAGTCC   2460
ACCCCTAGTC CCCACCTGGT GCCTTCACCT GCCCCATCTC CAGGGCCTGG TCCGGTACCC   2520
```

```
CCTCGCCCCC CAGCAGCAGA ACCACCCCCT TGCCTGCGCC GAGGCGCCGC AGCTGCAGAC    2580

CTGCTCTCCT CCAGCCCGGA GAGCCAGCAT GGCGGCACTC AGTCTCCTGG GGGTGGGCAG    2640

CCCCTGCTGC AGCCCACCAA GGTGGATGCA GCTGAGGGTC GTCGGCCGCA GGCCCTGCGG    2700

CTGATTGAGC GGGACCCCTA TGAGCATCCT GAGAGGCTGC GGCAGTTGCA GCAGGAGCTG    2760

GAGGCCTTTC GGGGTCAGCT GGGGGATGTG GGAGCTCTGG ACACTGTCTG GCGAGAGCTG    2820

CAAGATGCGC AGGAACATGA TGCCCGAGGC CGTTCCATCG CCATTGCCCG CTGCTACTCA    2880

CTGAAGAACC GGCACCAGGA TGTCATGCCC TATGACAGTA ACCGTGTGGT GCTGCGCTCA    2940

GGCAAGGATG ACTACATCAA TGCCAGCTGC GTGGAGGGGC TCTCCCCATA CTGCCCCCCG    3000

CTAGTGGCAA CCCAGGCCCC ACTGCCTGGC ACAGCTGCTG ACTTCTGGCT CATGGTCCAT    3060

GAGCAGAAAG TGTCAGTCAT TGTCATGCTG GTTTCTGAGG CTGAGATGGA GAAGCAAAAA    3120

GTGGCACGCT ACTTCCCCAC CGAGAGGGGC CAGCCCATGG TGCACGGTGC CCTGAGCCTG    3180

GCATTGAGCA GCGTCCGCAG CACCGAAACC CATGTGGAGC GCGTGCTGAG CCTGCAGTTC    3240

CGAGACCAGA GCCTCAAGCG CTCTCTTGTG CACCTGCACT TCCCCACTTG GCCTGAGTTA    3300

GGCCTGCCCG ACAGCCCCAG CAACTTGCTG CGCTTCATCC AGGAGGTGCA CGCACATTAC    3360

CTGCATCAGC GGCCGCTGCA CACGCCCATC ATTGTGCACT GCAGCTCTGG TGTGGGCCGC    3420

ACGGGAGCCT TTGCACTGCT CTATGCAGCT GTGCAGGAGG TGGAGGCTGG GAACGGAATC    3480

CCTGAGCTGC CTCAGCTGGT GCGGCGCATG CGGCAGCAGA GAAAGCACAT GCTGCAGGAG    3540

AAGCTGCACC TCAGGTTCTG CTATGAGGCA GTGGTGAGAC ACGTGGAGCA GGTCCTGCAG    3600

CGCCATGGTG TGCCTCCTCC ATGCAAACCC TTGGCCAGTG CAAGCATCAG CCAGAAGAAC    3660

CACCTTCCTC AGGACTCCCA GGACCTGGTC CTCGGTGGGG ATGTGCCCAT CAGCTCCATC    3720

CAGGCCACCA TTGCCAAGCT CAGCATTCGG CCTCCTGGGG GGTTGGAGTC CCCGGTTGCC    3780

AGCTTGCCAG GCCCTGCAGA GCCCCCAGGC CTCCCGCCAG CCAGCCTCCC AGAGTCTACC    3840

CCAATCCCAT CTTCCTCCCC ACCCCCCCTT TCCTCCCCAC TACCTGAGGC TCCCCAGCCT    3900

AAGGAGGAGC CGCCAGTGCC TGAAGCCCCC AGCTCGGGGC CCCCCTCCTC CTCCCTGGAA    3960

TTGCTGGCCT CCTTGACCCC AGAGGCCTTC TCCCTGGACA GCTCCCTGCG GGGCAAACAG    4020

CGGATGAGCA AGCATAACTT TCTGCAGGCC CATAACGGGC AAGGGCTGCG GGCCACCCGG    4080

CCCTCTGACG ACCCCCTCAG CCTTCTGGAT CCACTCTGGA CACTCAACAA GACCTGAACA    4140

GGTTTTGCCT ACCTGGTCCT TACACTACAT CATCATCATC TCATGCCCAC CTGCCCACAC    4200

CCAGCAGAGC TTCTCAGTGG GCACAGTCTC TTACTCCCAT TTCTGCTGCC TTTGGCCCTG    4260

CCTGGCCCAG CCTGCACCCC TGTGGGGTGG AAATGTACTG CAGGCTCTGG GTCAGGTTCT    4320

GCTCCTTTAT GGGACCCGAC ATTTTTCAGC TCTTTGCTAT TGAAATAATA AACCACCCTG    4380

TTCTGTGAAA AAAAAAAAAA AAAAAAAAAA AAAAAAAAAA AAAAAAAAAA AAAAAAAAAA    4440

AAAAAAAAAA AAAAA                                                   4456

(2) INFORMATION FOR SEQ ID NO: 2:

(i) SEQUENCE CHARACTERISTICS:
        (A) LENGTH:        1274 amino acids
        (B) TYPE:          amino acid
        (C) STRANDEDNESS:  single
        (D) TOPOLOGY:      linear (ii) MOLECULE TYPE:     peptide (xi) SEQUENCE DESCRIPTION: SEQ ID NO: 2:
```

```
Met Ala Ala His Glu Ala Ser Ser Leu Tyr Ser Glu Glu Lys Ala Lys
 1               5                   10                  15

Leu Leu Arg Glu Met Met Ala Lys Ile Glu Asp Lys Asn Glu Val Leu
            20                  25                  30

Asp Gln Phe Met Asp Ser Met Gln Leu Asp Pro Glu Thr Val Asp Asn
            35                  40                  45

Leu Asp Ala Tyr Ser His Ile Pro Pro Gln Leu Met Glu Lys Cys Ala
    50                  55                  60

Ala Leu Ser Val Arg Pro Asp Thr Val Arg Asn Leu Val Gln Ser Met
65              70                  75                  80

Gln Val Leu Ser Gly Val Phe Thr Asp Val Glu Ala Ser Leu Lys Asp
                85                  90                  95

Ile Arg Asp Leu Leu Glu Glu Asp Leu Leu Glu Gln Lys Phe Gln
            100                 105                 110

Glu Ala Val Gly Gln Ala Gly Ala Ile Ser Ile Thr Ser Lys Ala Glu
            115                 120                 125

Leu Ala Glu Val Arg Arg Glu Trp Ala Lys Tyr Met Glu Val His Glu
            130                 135                 140

Lys Ala Ser Phe Thr Asn Ser Glu Leu His Arg Ala Met Asn Leu His
145                 150                 155                 160

Val Gly Asn Leu Arg Leu Leu Ser Gly Pro Leu Asp Gln Val Arg Ala
                165                 170                 175

Ala Leu Pro Thr Pro Ala Leu Ser Pro Glu Asp Lys Ala Val Leu Gln
            180                 185                 190

Asn Leu Lys Arg Ile Leu Ala Lys Val Gln Glu Met Arg Asp Gln Arg
            195                 200                 205

Val Ser Leu Glu Gln Gln Leu Arg Glu Leu Ile Gln Lys Asp Asp Ile
210                 215                 220

Thr Ala Ser Leu Val Thr Thr Asp His Ser Glu Met Lys Lys Leu Phe
225                 230                 235                 240

Glu Glu Gln Leu Lys Lys Tyr Asp Gln Leu Lys Val Tyr Leu Glu Gln
                245                 250                 255

Asn Leu Ala Ala Gln Asp Arg Val Leu Cys Ala Leu Thr Glu Ala Asn
            260                 265                 270

Val Gln Tyr Ala Ala Val Arg Arg Val Leu Ser Asp Leu Asp Gln Lys
            275                 280                 285

Trp Asn Ser Thr Leu Gln Thr Leu Val Ala Ser Tyr Glu Ala Tyr Glu
            290                 295                 300

Asp Leu Met Lys Lys Ser Gln Glu Gly Arg Asp Phe Tyr Ala Asp Leu
305                 310                 315                 320

Glu Ser Lys Val Ala Ala Leu Leu Glu Arg Thr Gln Ser Thr Cys Gln
                325                 330                 335

Ala Arg Glu Ala Ala Arg Gln Gln Leu Leu Asp Arg Glu Leu Lys Lys
            340                 345                 350

Lys Pro Pro Arg Pro Thr Ala Pro Lys Pro Leu Leu Pro Arg Arg
            355                 360                 365

Glu Glu Ser Glu Ala Val Glu Ala Gly Asp Pro Glu Glu Leu Arg
            370                 375                 380

Ser Leu Pro Pro Asp Met Val Ala Gly Pro Arg Leu Pro Asp Thr Phe
385                 390                 395                 400

Leu Gly Ser Ala Thr Pro Leu His Phe Pro Ser Pro Phe Pro Ser
                405                 410                 415

Ser Thr Gly Pro Gly Pro His Tyr Leu Ser Gly Pro Leu Pro Pro Gly
```

-continued

```
                420                 425                 430
Thr Tyr Ser Gly Pro Thr Gln Leu Ile Gln Pro Arg Ala Pro Gly Pro
            435                 440                 445
His Ala Met Pro Val Ala Pro Gly Pro Ala Leu Tyr Pro Ala Pro Ala
    450                 455                 460
Tyr Thr Pro Glu Leu Gly Leu Val Pro Arg Ser Ser Pro Gln His Gly
465                 470                 475                 480
Val Val Ser Ser Pro Tyr Val Gly Val Gly Pro Ala Pro Pro Val Ala
                485                 490                 495
Gly Leu Pro Ser Ala Pro Pro Gln Phe Ser Gly Pro Glu Leu Ala
                500                 505                 510
Met Ala Val Arg Pro Ala Thr Thr Thr Val Asp Ser Ile Gln Ala Pro
            515                 520                 525
Ile Pro Ser His Thr Ala Pro Arg Pro Asn Pro Thr Pro Ala Pro Pro
    530                 535                 540
Pro Pro Cys Phe Pro Val Pro Pro Gln Pro Leu Pro Thr Pro Tyr
545                 550                 555                 560
Thr Tyr Pro Ala Gly Ala Lys Gln Pro Ile Pro Ala Gln His His Phe
                565                 570                 575
Ser Ser Gly Ile Pro Thr Gly Phe Pro Ala Pro Arg Ile Gly Pro Gln
                580                 585                 590
Pro Gln Pro His Pro Gln Pro His Pro Ser Gln Ala Phe Gly Pro Gln
            595                 600                 605
Pro Pro Gln Gln Pro Leu Pro Leu Gln His Pro His Leu Phe Pro Pro
    610                 615                 620
Gln Ala Pro Gly Leu Leu Pro Gln Ser Pro Tyr Pro Tyr Ala Pro
625                 630                 635                 640
Gln Pro Gly Val Leu Gly Gln Pro Pro Pro Leu His Thr Gln Leu
                645                 650                 655
Tyr Pro Gly Pro Ala Gln Asp Pro Leu Pro Ala His Ser Gly Ala Leu
                660                 665                 670
Pro Phe Pro Ser Pro Gly Pro Pro Gln Pro Pro His Pro Pro Leu Ala
            675                 680                 685
Tyr Gly Pro Ala Pro Ser Thr Arg Pro Met Gly Pro Gln Ala Ala Pro
    690                 695                 700
Leu Thr Ile Arg Gly Pro Ser Ser Ala Gly Gln Ser Thr Pro Ser Pro
705                 710                 715                 720
His Leu Val Pro Ser Pro Ala Pro Ser Pro Gly Pro Gly Pro Val Pro
                725                 730                 735
Pro Arg Pro Pro Ala Ala Glu Pro Pro Cys Leu Arg Arg Gly Ala
            740                 745                 750
Ala Ala Ala Asp Leu Leu Ser Ser Pro Glu Ser Gln His Gly Gly
            755                 760                 765
Thr Gln Ser Pro Gly Gly Gln Pro Leu Leu Gln Pro Thr Lys Val
    770                 775                 780
Asp Ala Ala Glu Gly Arg Arg Pro Gln Ala Leu Arg Leu Ile Glu Arg
785                 790                 795                 800
Asp Pro Tyr Glu His Pro Glu Arg Leu Arg Gln Leu Gln Gln Glu Leu
                805                 810                 815
Glu Ala Phe Arg Gly Gln Leu Gly Asp Val Gly Ala Leu Asp Thr Val
                820                 825                 830
Trp Arg Glu Leu Gln Asp Ala Gln Glu His Asp Ala Arg Gly Arg Ser
            835                 840                 845
```

```
Ile Ala Ile Ala Arg Cys Tyr Ser Leu Lys Asn Arg His Gln Asp Val
850                 855                 860
Met Pro Tyr Asp Ser Asn Arg Val Val Leu Arg Ser Gly Lys Asp Asp
865                 870                 875                 880
Tyr Ile Asn Ala Ser Cys Val Glu Gly Leu Ser Pro Tyr Cys Pro Pro
                885                 890                 895
Leu Val Ala Thr Gln Ala Pro Leu Pro Gly Thr Ala Ala Asp Phe Trp
                900                 905                 910
Leu Met Val His Glu Gln Lys Val Ser Val Ile Val Met Leu Val Ser
                915                 920                 925
Glu Ala Glu Met Glu Lys Gln Lys Val Ala Arg Tyr Phe Pro Thr Glu
930                 935                 940
Arg Gly Gln Pro Met Val His Gly Ala Leu Ser Leu Ala Leu Ser Ser
945                 950                 955                 960
Val Arg Ser Thr Glu Thr His Val Glu Arg Val Leu Ser Leu Gln Phe
                965                 970                 975
Arg Asp Gln Ser Leu Lys Arg Ser Leu Val His Leu His Phe Pro Thr
                980                 985                 990
Trp Pro Glu Leu Gly Leu Pro Asp Ser Pro Ser Asn Leu Leu Arg Phe
            995                 1000                1005
Ile Gln Glu Val His Ala His Tyr Leu His Gln Arg Pro Leu His Thr
            1010                1015                1020
Pro Ile Ile Val His Cys Ser Ser Gly Val Gly Arg Thr Gly Ala Phe
1025                1030                1035                1040
Ala Leu Leu Tyr Ala Ala Val Gln Glu Val Glu Ala Gly Asn Gly Ile
                1045                1050                1055
Pro Glu Leu Pro Gln Leu Val Arg Arg Met Arg Gln Gln Arg Lys His
                1060                1065                1070
Met Leu Gln Glu Lys Leu His Leu Arg Phe Cys Tyr Glu Ala Val Val
                1075                1080                1085
Arg His Val Glu Gln Val Leu Gln Arg His Gly Val Pro Pro Pro Cys
                1090                1095                1100
Lys Pro Leu Ala Ser Ala Ser Ile Ser Gln Lys Asn His Leu Pro Gln
1105                1110                1115                1120
Asp Ser Gln Asp Leu Val Leu Gly Gly Asp Val Pro Ile Ser Ser Ile
                1125                1130                1135
Gln Ala Thr Ile Ala Lys Leu Ser Ile Arg Pro Pro Gly Gly Leu Glu
                1140                1145                1150
Ser Pro Val Ala Ser Leu Pro Gly Pro Ala Glu Pro Pro Gly Leu Pro
                1155                1160                1165
Pro Ala Ser Leu Pro Glu Ser Thr Pro Ile Pro Ser Ser Ser Pro Pro
                1170                1175                1180
Pro Leu Ser Ser Pro Leu Pro Glu Ala Pro Gln Pro Lys Glu Glu Pro
1185                1190                1195                1200
Pro Val Pro Glu Ala Pro Ser Ser Gly Pro Pro Ser Ser Ser Leu Glu
                1205                1210                1215
Leu Leu Ala Ser Leu Thr Pro Glu Ala Phe Ser Leu Asp Ser Ser Leu
                1220                1225                1230
Arg Gly Lys Gln Arg Met Ser Lys His Asn Phe Leu Gln Ala His Asn
                1235                1240                1245
Gly Gln Gly Leu Arg Ala Thr Arg Pro Ser Asp Asp Pro Leu Ser Leu
                1250                1255                1260
```

```
Leu Asp Pro Leu Trp Thr Leu Asn Lys Thr
1265                1270
```

(2) INFORMATION FOR SEQ ID NO: 3:

(i) SEQUENCE CHARACTERISTICS:
        (A) LENGTH:          23 base pairs
        (B) TYPE:            nucleic acid
        (C) STRANDEDNESS:    single
        (D) TOPOLOGY:        linear (ix) FEATURE:
        (D) OTHER INFORMATION:   The letter "Y" stands for C or T.
            The letter "V" stands for A, C or G.
            The letter "R" stands for A or G.
            The letter "N" stands for A, C, G or T.

(xi) SEQUENCE DESCRIPTION: SEQ ID NO: 3:

```
GAYTTYTGGV RNATGRTNTG GGA                                             23
```

(2) INFORMATION FOR SEQ ID NO: 4:

(i) SEQUENCE CHARACTERISTICS:
        (A) LENGTH:          23 base pairs
        (B) TYPE:            nucleic acid
        (C) STRANDEDNESS:    single
        (D) TOPOLOGY:        linear (ix) FEATURE:
        (D) OTHER INFORMATION:   The letter "S" stands for C or G.
            The letter "Y" stands for C or T.
            The letter "N" stands for A, C, G or T.
            The letter "W" stands for A or T.
            The letter "R" stands for A or G.

(xi) SEQUENCE DESCRIPTION: SEQ ID NO: 4:

```
CGGCCSAYNC CNGCNSWRCA RTG                                             23
```

(2) INFORMATION FOR SEQ ID NO: 5:

(i) SEQUENCE CHARACTERISTICS:
        (A) LENGTH:          26 base pairs
        (B) TYPE:            nucleic acid
        (C) STRANDEDNESS:    single
        (D) TOPOLOGY:        linear (ix) FEATURE:
        (D) OTHER INFORMATION:   The letter "Y" stands for C or T.
            The letter "H" stands for A, C or T.
            The letter "M" stands for A or C.

(xi) SEQUENCE DESCRIPTION: SEQ ID NO: 5:

```
ATCCCCGGCT CTGAYTAYAT HMAYGC                                          26
```

(2) INFORMATION FOR SEQ ID NO: 6:

(i) SEQUENCE CHARACTERISTICS:
        (A) LENGTH:          8 amino acids
        (B) TYPE:            amino acid
        (C) STRANDEDNESS:    single
        (D) TOPOLOGY:        linear (ii) MOLECULE TYPE:        Peptide (ix) FEATURE:
        (D) OTHER INFORMATION:   "Xaa" in positions 4 and 6 stand for
            an unspecified amino acid. "Xaa" in position 8 stands for
            either Glu or Asp.

(xi) SEQUENCE DESCRIPTION: SEQ ID NO: 6:

```
Asp Phe Trp Xaa Met Xaa Trp Xaa
```

```
(2) INFORMATION FOR SEQ ID NO: 7:

(i) SEQUENCE CHARACTERISTICS:
        (A) LENGTH:          7 amino acids
        (B) TYPE:            amino acid
        (C) STRANDEDNESS:    single
        (D) TOPOLOGY:        linear (ii) MOLECULE TYPE:      Peptide (ix) FEATURE:
        (D) OTHER INFORMATION:  "Xaa" in positions 3 and 6 stand for
            an unspecified amino acid.

(xi) SEQUENCE DESCRIPTION: SEQ ID NO: 7:

His Cys Xaa Ala Gly Xaa Gly
1               5

(2) INFORMATION FOR SEQ ID NO: 8:

(i) SEQUENCE CHARACTERISTICS:
        (A) LENGTH:          9 amino acids
        (B) TYPE:            amino acid
        (C) STRANDEDNESS:    single
        (D) TOPOLOGY:        linear (ii) MOLECULE TYPE:      peptide (ix) FEATURE:
        (D) OTHER INFORMATION:  "Xaa" in position 8 stands for either
            Asn or His.

(xi) SEQUENCE DESCRIPTION: SEQ ID NO: 8:

Ile Pro Gly Ser Asp Tyr Ile Xaa Ala
1               5
```

DIAGNOSIS AND TREATMENT OF ALP RELATED DISORDERS

RELATED APPLICATIONS

This application claims priority to the U.S. Provisional Patent Application No. 60/049,477, by Plowman et al., entitled "Diagnosis and Treatment of ALP Related Disorders," and filed Jun. 11, 1997, which is incorporated herein by reference in its entirety, including any drawings.

FIELD OF THE INVENTION

The present invention relates to tyrosine phosphatases. In particular, the invention concerns a protein we have named ALP (Adaptor Like Phosphatase), nucleotide sequences encoding ALP, various products and assay methods that can be used for identifying compounds useful for the diagnosis and treatment of various ALP-related diseases and conditions, for example cell proliferative disorders.

BACKGROUND OF THE INVENTION

The following description is provided to aid in understanding the invention but is not admitted to be prior art to the invention.

Cellular signal transduction is a fundamental mechanism whereby external stimuli that regulate diverse cellular processes are relayed to the interior of cells. One of the key biochemical mechanisms of signal transduction involves the reversible phosphorylation of proteins, which enables regulation of the activity of mature proteins by altering their structure and function. The best characterized protein kinases in eukaryotes phosphorylate proteins on the alcohol moiety of serine, threonine and tyrosine residues. These kinases largely fall into two groups, those specific for phosphorylating serines and threonines, and those specific for phosphorylating tyrosines.

The phosphorylation state of a given substrate is also regulated by a class of proteins responsible for removal of the phosphate group added to a given substrate by a protein kinase. The protein phosphatases can also be classified as being specific for either serine/threonine or tyrosine. The known enzymes can be divided into two groups—receptor and non-receptor type proteins. Most receptor-type protein tyrosine phosphatases (RPTPs) contain two conserved catalytic tyrosine phosphatase domains each of which encompasses a segment of 240 amino acid residues (Saito et al; *Cell Growth and Diff.* 2:59–65, 1991). The RPTPs can be subclassified further based upon the amino acid sequence diversity of their extracellular domains (Saito, et al; supra; Krueger, et al; *Proc. Natl. Acad. Sci. USA* 89:7417–7421, 1992).

Alignment of primary peptide sequences of both types of known PTPases shows some sequence consensus in catalytic domains and has made it possible to identify cDNAs encoding proteins with tyrosine phosphate activIty via the polymerase chain reaction (PCR).

Many kinases and phosphatases are involved in regulatory cascades wherein their substrates may include, but are not limited to, other kinases and phosphatases whose activities are regulated by their phosphorylation state. Ultimately the activity of some downstream effector is modulated by phosphorylation resulting from activation of such a pathway.

Tyrosine phosphatases have been thought to be possible candidate cancer causing proteins. Inappropriate activity through overexpression of RPTP-alpha, for example, has been associated with colon cancer (Pallen, et al, WO 94/01119, published Jan. 20, 1994). A need exists to identify additional proteins whose inappropriate activity may lead to cancer or other disorders so that pharmaceutical compounds for the treatment of those disorders might also be identified.

SUMMARY OF THE INVENTION

Disclosed herein is a tyrosine phosphatase overexpressed in cancer cells which we have named ALP. The properties of ALP are described below. The present invention concerns ALP polypeptides, nucleic acids encoding such polypeptides, cells, tissues and animals containing such nucleic acids, antibodies to the polypeptides, assays utilizing the polypeptides, and methods relating to all of the foregoing.

A first aspect of the invention features an isolated, enriched, or purified nucleic acid molecule encoding an ALP polypeptide.

By "isolated" in reference to nucleic acid it is meant a polymer of 14, 17, 21 or more nucleotides conjugated to each other, including DNA or RNA that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide sequence present, but that it is essentially free (about 90–95% pure at least) of nucleotide material naturally associated with it and thus is meant to be distinguished from isolated chromosomes.

By the use of the term "enriched" in reference to nucleic acid it is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

The term "significant" here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The other source DNA may, for example, comprise DNA from a yeast or bacterial genome, or a cloning vector such as pUC19. This term distinguishes the sequence from naturally occurring enrichment events, such as viral infection, or tumor type growths, in which the level of one mRNA may be naturally increased relative to other species of mRNA. That is, the term is meant to cover only those situations in which a person has intervened to elevate the proportion of the desired nucleic acid.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level this level should be at least 2–5 fold greater, e.g., in terms of mg/mL). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated. The term is also chosen to distinguish clones already in existence which may encode ALP but which have not been isolated from other clones in a library of clones. Thus, the term covers clones encoding ALP which are isolated from other non-ALP clones.

The term "nucleic acid molecule" describes a polymer of deoxyribonucleotides (DNA) or ribonucleotides (RNA). The nucleic acid molecule may be isolated from a natural source by cDNA cloning or subtractive hybridization or synthesized manually. The nucleic acid molecule may be synthesized manually by the triester synthetic method or by using an automated DNA synthesizer.

The term "cDNA cloning" refers to hybridizing a small nucleic acid molecule, a probe, to genomic cDNA. The probe hybridizes (binds) to complementary sequences of cDNA.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

The term "hybridize" refers to a method of interacting a nucleic acid sequence with a DNA or RNA molecule in solution or on a solid support, such as cellulose or nitrocellulose. If a nucleic acid sequence binds to the DNA or RNA molecule with high affinity, it is said to "hybridize" to the DNA or RNA molecule. The strength of the interaction between the probing sequence and its target can be assessed by varying the stringency of the hybridization conditions. Under highly stringent hybrydization conditions only highly complementary nucleic acid sequences hybridize. Preferably, such conditions prevent hybridization of nucleic acids having one or two mismatches out of 20 contiguous nucleotides.

Various low or high stringency hybridization conditions may be used depending upon the specificity and selectivity desired. Stringency is controlled by varying salt or denaturant concentrations. Examples of hybridization conditions are shown in the examples below. High stringent conditions may mean conditions that are at least as stringent as the following: hybridization in 50% formamide, 5×SSC, 50 mM $NaH_3PO_4$, pH 6.8, 0.5t SDS, 0.1 mg/mL sonicated salmon sperm DNA, and 5×Denhart solution at 42° C. overnight; washing with 2×SSC, 0.1% SDS at 45° C.; and washing with 0.2×SSC, 0.1% SDS at 45° C. Those skilled in the art will recognize how such conditions can be varied to vary specificity and selectivity.

An ALP polypeptide can be encoded by a full-length nucleic acid sequence or any portion of the full-length nucleic acid sequence. In preferred embodiments the isolated nucleic acid comprises, consists essentially of, or consists of a nucleic acid sequence set forth in SEQ ID NO:1, a nucleic acid sequence that hybidizes to the nucleic acid sequence set forth in SEQ ID NO:1 or a functional derivative (as defined below) of either. The nucleic acid may be isolated from a natural source by cDNA cloning or subtractive hybridization; the natural source may be mammalian (human) blood, semen, or tissue and the nucleic acid may be synthesized by the triester or other method or by using an automated DNA synthesizer.

The term "mammalian" refers to such organisms as mice, rats, rabbits, goats, more preferably monkeys and apes, and most preferably humans.

In other preferred embodiments, the nucleic acid molecule of the invention comprises a nucleotide sequence that (a) encodes a polypeptide having the full length amino acid sequence set forth in SEQ ID NO:2; (b) is the complement of the nucleotide sequence of (a); (c) hybridizes under highly stringent conditions to the nucleotide molecule of (a) and encodes a naturally occurring ALP polypeptide; (d) encodes an ALP polypeptide having the full length amino acid sequence of the sequence set forth in SEQ ID NO:2, except that it lacks one or more of the following segments of amino acid residues: 1–857, 353–777, 858–1096, 1097–1274, 1101–1214 of SEQ ID NO:2; (e) is the complement of the nucleotide sequence of (d); (f) encodes a polypeptide having the amino acid sequence set forth in SEQ ID NO:2 from amino acid residues 1–857, 353–777, 858–1096, 1097–1274, 1101–1214 of SEQ ID NO:2; (g) is the complement of the nucleotide sequence of (f); (h) encodes a polypeptide having the full length amino acid sequence set forth in SEQ ID NO:2, except that it lacks one or more of the domains selected from the group consisting of an N-terminal domain, an N-terminal proline-rich domain, a catalytic domain, a C-terminal proline/serine-rich domain, and a C-terminal domain; or (i) is the complement of the nucleotide sequence of (h). The nucleic acid molecule of the invention is isolated, enriched, or purified from, preferably, a mammal, or most preferably from a human.

In yet other preferred embodiments the nucleic acid is an isolated conserved or unique region, for example those useful for the design of hybridization probes to facilitate identification and cloning of additional polypeptides, or for the design of PCR probes to facilitate cloning of additional polypeptides.

By "conserved nucleic acid regions", it is meant regions present on two or more nucleic acids encoding an ALP polypeptide, to which a particular nucleic acid sequence can hybridize under lower stringency conditions. Examples of lower stringency conditions suitable for screening for nucleic acids encoding ALP polypeptides are provided in Abe, et al. *J. Biol. Chem.* 19:13361 (1992) (hereby incorporated by reference herein in its entirety, including any drawings). Preferably, conserved regions differ by no more than 5 out of 20 continguous nucleotides.

By "unique nucleic acid region" it is meant a sequence present in a full length nucleic acid coding for an ALP polypeptide that is not present in a sequence coding for any other known naturally occurring polypeptide. Such regions preferably comprise 14, 17, 21 or more contiguous nucleotides present in the full length nucleic acid encoding an ALP polypeptide. In particular, a unique nucleic acid region is preferably of human origin.

In yet another aspect, the invention relates to a nucleic acid vector comprising a nucleic acid molecule encoding an ALP polypeptide and a promoter element effective to initiate transcription in a host cell.

The term "nucleic acid vector" relates to a single or double stranded circular nucleic acid molecule that can be transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that the restriction enzymes operate upon are readily available to those skilled in the art. A nucleic acid molecule of the invention can be inserted into a vector by cutting the vector with restriction enzymes and ligating the two pieces together.

Many techniques are available to those skilled in the art to facilitate transformation or transfection of the expression construct into a prokaryotic or eukaryotic organism. The terms "transformation" and "transfection" refer to methods of inserting an expression construct into a cellular organism. These methods involve a variety of techniques, such as treating the cells with high concentrations of salt, an electric field, or detergent, to render the host cell outer membrane or wall permeable to nucleic acid molecules of interest.

The term "promoter element" describes a nucleotide sequence that is incorporated into a vector that, once inside an appropriate cell, can facilitate transcription factor and/or polymerase binding and subsequent transcription of portions of the vector DNA into mRNA. The promoter element precedes the 5' end of the ALP nucleic acid molecule such that the latter is transcribed into mRNA. Host cell machinery then translates mRNA into a polypeptide.

Those skilled in the art would recognize that a nucleic acid vector can contain many other nucleic acid elements besides the promoter element and the ALP nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, periplasm or peroxisome localization signals, or signals useful for polypeptide purification.

The invention also features a nucleic acid probe for the detection of a nucleic acid encoding an Alp polypeptide in a sample. The term "nucleic acid probe" refers to a nucleic acid molecule that is complementary to and can bind a nucleic acid sequence encoding the amino acid sequence substantially similar to that set forth in SEQ ID NO:2.

The nucleic acid probe contains nucleic acid that will hybridize specifically to a sequence of at least 14, preferably 17, 20 or 22, contiguous nucleotides set forth in SEQ ID NO:1 or a functional derivative thereof. The probe is preferably at least 14, 17 or more bases in length and selected to hybridize specifically to a unique region of an ALP endocing nucleic acid.

In preferred embodiments the nucleic acid probe hybridizes to nucleic acid encoding at least 14 contiguous amino acids of the full-length sequence set forth in SEQ ID NO:1 or a functional derivative thereof. Various low or high stringency hybridization conditions may be used depending upon the specificity and selectivity desired. Under highly stringent hybridization conditions only highly complementary nucleic acid sequences hybridize. Preferably, such conditions prevent hybridization of nucleic acids having 1 or 2 mismatches out of 20 contiguous nucleotides.

Methods for using the probes include detecting the presence or amount of ALP RNA in a sample by contacting the sample with a nucleic acid probe under conditions such that hybridization occurs and detecting the presence or amount of the probe bound to ALP RNA. The nucleic acid duplex formed between the probe and a nucleic acid sequence coding for an ALP polypeptide may be used in the identification of the sequence of the nucleic acid detected (for example see, Nelson et al., in Nonisotopic DNA Probe Techniques, p. 275 Academic Press, San Diego (Kricka, ed., 1992) hereby incorporated by reference herein in its entirety, including any drawings). Kits for performing such methods may be constructed to include a container having disposed therein a nucleic acid probe.

Another feature of the invention is a nucleic acid molecule as set forth in SEQ ID NO:1 or fragments thereof, comprising one or more regions that encode an ALP polypeptide or an ALP domain polypeptide, where the ALP polypeptide or the ALP domain polypeptide is fused to a non-ALP polypeptide. Such fused polypeptides include, for example, but are not limited to, a GST-fusion protein.

The invention also features recombinant nucleic acid, preferably in a cell or an organism. The recombinant nucleic acid may contain a sequence set forth in SEQ ID NO:1 or a functional derivative thereof and a vector or a promoter effective to initiate transcription in a host cell. The recombinant nucleic acid can alternatively contain a transcriptional initiation region functional in a cell, a sequence complimentary to an RNA sequence encoding an ALP polypeptide and a transcriptional termination region functional in a cell.

Another aspect of the invention relates to a recombinant cell or tissue comprising a nucleic acid molecule encoding an ALP polypeptide. The recombinant cell may comprise a nucleic acid molecule encoding either an ALP polypeptide; an ALP domain polypeptide; or an ALP polypeptide or ALP domain polypeptide fused to a non-ALP polypeptide.

The term "recombinant organism" refers to an organism that has a new combination of genes or nucleic acid molecules. A new combination of genes or nucleic acid molecules can be introduced to an organism using a wide array of nucleic acid manipulation techniques available to those skilled in the art.

The term "organism" relates to any living being comprised of a least one cell. An organism can be as simple as one eukaryotic cell or as complex as a mammal. Therefore, a recombinant organism can also be a recombinant cell, which may be a eukaryotic or a prokaryotic organism.

The term "eukaryote" refers to an organism comprised of cells that contain a nucleus. Eukaryotes are differentiated from "prokaryotes" which do not have a nucleus and lack other cellular structures found in eukaryotes, such as mitochondria and endoplasmic reticulum. Prokaryotes include unicellular organisms, such as bacteria, while eukaryotes are represented by yeast, invertebrates, and vertebrates.

The recombinant cell can harbor a nucleic acid vector that is extragenomic. The term "extragenomic" refers to a nucleic acid vector which does not insert into the cell genome. Many nucleic acid vectors are designed with their own origins of replication allowing them to utilize the recombinant cell replication machinery to copy and propagate the vector nucleic acid sequence. These vectors are small enough that they are not likely to harbor nucleic acid sequences homologous to genomic sequences of the recombinant cell. Thus these vectors replicate independently of the host genome and do not recombine with or integrate into the genome.

A recombinant cell can harbor a portion of a nucleic acid vector in an intragenomic fashion. The term "intragenomic" defines a nucleic acid construct that is incorporated within the cell genome. Multiple nucleic acid vectors available to those skilled in the art contain nucleic acid sequences that are homologous to nucleic acid sequences in a particular organism's genomic DNA. These homologous sequences will result in recombination events that integrate portions of the vector into the genomic DNA. Those skilled in the art can control which nucleic acid sequences of the vector are integrated into the cell genome by flanking the portion to be incorporated into the genome with homologous sequences in the vector.

Another aspect of the invention features an isolated, enriched, or purified ALP polypeptide.

By "ALP polypeptide" it is meant an amino acid sequence substantially similar to the sequence shown in SEQ ID NO:2, or fragments thereof. A sequence that is substantially similar will preferably have at least 90% identity (more preferably at least 95% and most preferably 99–100%) to the sequence of SEQ ID NO:2.

The ALP polypeptides of the present invention preferably have a substantially similar biological activity to the protein encoded by the full length nucleic acid sequence set forth in SEQ ID NO:1 or to the proteins with amino acid sequence set forth in SEQ ID NO:2. By "biological activity" it is meant an activity of the ALP protein in a cell. The biological activity of the ALP is related to some of the activities of the cell which include, but are not limited to, cell proliferation motogenesis, metastasis, tumor escape, cell adhesion, transformation, or apoptosis.

By "identity" is meant a property of sequences that measures their similarity or relationship. Identity is measured by dividing the number of identical residues in the two sequences by the total number of residues and multiplying the product by 100. Thus, two copies of exactly the same sequence have 100% identity, but sequences that are less highly conserved and have deletions, additions, or replacements have a lower degree of identity. Those skilled in the art will recognize that several computer programs are available for determining sequence identity.

By "isolated" in reference to a polypeptide is meant a polymer of 6, 12, 18 or more amino acids conjugated to each other, including polypeptides that are isolated from a natural source or that are synthesized. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is essentially free (about 90–95% pure at least) of material naturally associated with it.

By the use of the term "enriched" in reference to a polypeptide it is meant that the specific amino acid sequence constitutes a significantly higher fraction (2–5 fold) of the total of amino acid sequences present in the cells or solution of interest than in normal or diseased cells or in the cells from which the sequence was taken. This could be caused by a person by preferential reduction in the amount of other amino acid sequences present, or by a preferential increase in the amount of the specific amino acid sequence of interest, or by a combination of the two. However, it should be noted that "enriched" does not imply that there are no other amino acid sequences present, just that the relative amount of the sequence of interest has been significantly increased.

The term "significant" here is used to indicate that the level of increase is useful to the person making such an increase, and generally means an increase relative to other amino acid sequences of about at least 2 fold, more preferably at least 5 to 10 fold or even more. The term also does not imply that there are no amino acid sequences from other sources. The other source amino acid may, for example, comprise amino acid sequences encoded by a yeast or bacterial genome, or a cloning vector such as pUC19. The term is meant to cover only those situations in which a person has intervened to elevate the proportion of the desired nucleic acid.

It is also advantageous for some purposes that an amino acid sequence be in purified form. The term "purified" in reference to a polypeptide does not require absolute purity (such as a homogeneous preparation); instead, it represents an indication that the sequence is relatively purer than in the natural environment (compared to the natural level this level should be at least 2–5 fold greater, e.g., in terms of mg/mL). Purification of at least one order of magnitude, preferably two or three orders, and more preferably four or five orders of magnitude is expressly contemplated. The substance is preferably free of contamination at a functionally significant level, for example 90%, 95%, or 99% pure.

In another aspect the invention features an isolated, enriched, or purified ALP polypeptide fragment.

By "an ALP polypeptide fragment" it is meant an amino acid sequence that is less than the full-length ALP amino acid sequence shown in SEQ ID NO:2. Examples of fragments include ALP domains, ALP mutants and ALP-specific epitopes.

By "an ALP domain" it is meant a portion of the ALP polypeptide having homology to amino acid sequences from one or more known proteins wherein the sequence predicts some common function, interaction or activity. Well known examples of domains are the SH2 (Src Homology 2) domain (Sadowski, et al., *Mol. Cell. Biol.* 6:4396, 1986; Pawson and Schlessinger, *Curr. Biol.* 3:434, 1993), the SH3 domain (Mayer, et al., *Nature* 332:272, 1988; Pawson and Schlessinger, *Curr. Biol.* 3:434, 1993), and pleckstrin (PH) domain (Ponting, *TIBS* 21:245, 1996; Haslam, et al., *Nature* 363:309, 1993), all of which are domains that mediate protein:protein interaction, and the kinase catalytic domain (Hanks and Hunter, *FASEB J* 9:576–595, 1995). Computer programs designed to detect such homologies are well known in the art. The relative homology is at least 20%, more preferably at least 30% and most preferably at least 35%.

By a "ALP mutant" it is meant an ALP polypeptide which differs from the native sequence in that one or more amino acids have been changed, added or deleted. Changes in amino acids may be conservative or non-conservative. By "conservative" it is meant the substitution of an amino acid for one with similar properties such as charge, hydrophobicity, structure, etc. Examples of polypeptides encompased by this term include, but are not limited to, (1) chimeric proteins which comprise a portion of an ALP polypeptide sequence fused to a non-ALP polypeptide sequence, for example a polypeptide sequence of hemmaglutinin (HA), (2) ALP proteins lacking a specific domain, for example the catalytic domain, and (3) ALP proteins having a point mutation. An ALP mutant will retain some useful function such as, for example, binding to a natural binding partner, catalytic activity, or the ability to bind to an ALP specific antibody (as defined below).

By "ALP-specific epitope" it is meant a sequence of amino acids that is both antigenic and unique to ALP. ALP-specific epitope can be used to produce ALP-specific antibodies, as more fully described below. A particularly preferred sequence is amino acids 1 to 352 of SEQ ID NO:2.

By "recombinant ALP polypeptide" it is meant to include a polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature.

The polypeptide of the invention comprises an amino acid sequence having (a) the full length amino acid sequence set forth in SEQ ID NO:2; (b) the full length amino acid sequence of the sequence set forth in SEQ ID NO:2, except that it lacks one or more of the following segments of amino acid residues: 1–857, 353–777, 858–1096, 1097–1274, 1101–1214 of SEQ ID NO:2; (c) the amino acid sequence set forth in SEQ ID NO:2 from amino acid residues, 1–857, 353–777, 858–1096, 1097–1274, 1101–1214 of SEQ ID NO:2; or (d) the full length amino acid sequence set forth in SEQ ID NO:2 except that it lacks one or more of the domains selected from the group consisting of an N-terminal domain, an N-terminal proline-rich domain, a catalytic domain, a C-terminal proline/serine-rich domain, and a C-terminal domain.

In yet another aspect the invention features an antibody (e.g., a monoclonal or polyclonal antibody) having specific binding affinity to an ALP polypeptide or ALP polypeptide fragment. By "specific binding affinity" is meant that the antibody binds to target (ALP) polypeptides with greater affinity than it binds to other polypeptides under specified conditions. Antibodies having specific binding affinity to an ALP polypeptide may be used in methods for detecting the presence and/or amount of an ALP polypeptide in a sample by contacting the sample with the antibody under conditions such that an immunocomplex forms and detecting the presence and/or amount of the antibody conjugated to the ALP polypeptide. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

The term "polyclonal" refers to antibodies that are heterogenous populations of antibody molecules derived from the sera of animals immunized with an antigen or an antigenic functional derivative thereof. For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, for example, Kohler, et al., Nature 256:495–497 (1975), and U.S. Pat. No. 4,376, 110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

In another aspect the invention features a hybridoma which produces an antibody having specific binding affinity to an ALP polypeptide. By "hybridoma" is meant an immortalized cell line which is capable of secreting an antibody, for example an ALP antibody. In preferred embodiments the ALP antibody comprises a sequence of amino acids that is able to specifically bind an ALP polypeptide.

The invention features a method for identifying human cells containing an ALP polypeptide or a related sequence. The method involves identifying the novel polypeptide in human cells using techniques that are routine and standard in the art, such as those described herein for identifying ALP (e.g., cloning, Southern or Northern blot analysis, in situ hybridization, PCR amplification, etc.).

The invention also features methods of screening cells for natural binding partners of ALP polypeptides. By "natural binding partner" it is meant a protein that interacts with ALP. Binding partners include ligands, agonists, antagonists and downstream signaling molecules such as adaptor proteins and may be identified by techniques well known in the art such as co-immunoprecipitation or by using, for example, a two-hybrid screen. (Fields and Song, U.S. Pat. No. 5,283, 173, issued Feb. 1, 1994 and, incorporated be reference herein.) The present invention also features the purified, isolated or enriched versions of the polypeptides identified by the methods described above.

In another aspect, the invention provides a method for identifying a substance capable of modulating ALP activity comprising the steps of (a) contacting an ALP polypeptide with a test substance; and (b) determining whether the substance alters the activity of said polypeptide.

The invention also features another method of identifying substances capable of modulating the function of a polypeptide. The method comprises the following steps: (a) expressing an ALP polypeptide in cells; (b) adding a compound to the cells; and (c) monitoring a change or an absence of a change in cell phenotype, cell proliferation, catalytic activity of the ALP polypeptide, and binding a natural binding partner.

The term "compound" includes small organic molecules including, but not limited to, oxindolinones, quinazolines, tyrphostins, quinoxalines, and those contained within extracts from natural sources. Examples of such compounds are included in section XII, below.

The term "function" refers to the cellular role of a serine-threonine protein kinase. The serine-threonine protein kinase family includes members that regulate many steps in signaling cascades, including cascades controlling cell growth, migration, differentiation, gene expression, muscle contraction, glucose metabolism, cellular protein synthesis, and regulation of the cell cycle.

The term "modulates" refers to the ability of a compound to alter the function of a protein kinase. A modulator preferably activates the catalytic activity of a protein kinase, more preferably activates or inhibits the catalytic activity of a protein kinase depending on the concentration of the compound exposed to the protein kinase, or most preferably inhibits the catalytic activity of a protein kinase.

The term "catalytic activity," in the context of the invention, defines the ability of a protein kinase to phosphorylate a substrate. Catalytic activity can be measured, for example, by determining the amount of a substrate converted to a product as a function of time. Phosphorylation of a substrate occurs at the active-site of a protein kinase. The active-site is normally a cavity in which the substrate.

The term "substrate" as used herein refers to a molecule that is phosphorylated by or directly interacts with the protein kinase. The substrate is preferably a peptide and more preferably a protein. For example, in relation to the protein kinase RAF, preferred substrates are MEK and the MEK substrate MAPK.

The term "activates" refers to increasing the cellular function of a protein kinase. The protein kinase function is preferably the interaction with a natural binding partner or catalytic activity.

The term "inhibit" refers to decreasing the cellular function of a protein kinase. The protein kinase function is preferably the interaction with a natural binding partner or catalytic activity.

The term "modulates" also refers to altering the function of a protein kinase by increasing or decreasing the probability that a complex forms between a protein kinase and a natural binding partner. A modulator preferably increases the probability that such a complex forms between the protein kinase and the natural binding partner, more preferably increases or decreases the probability that a complex forms between the protein kinase and the natural binding partner depending on the concentration of the compound exposed to the protein kinase, and most preferably decreases the probability that a complex forms between the protein kinase and the natural binding partner.

The term "complex" refers to an assembly of at least two molecules bound to one another. Signal transduction complexes often contain at least two protein molecules bound to one another, either transiently or in succession. For instance, a receptor protein tyrosine kinase, GRB2, SOS, and RAF sequentially interact in response to a mitogenic ligand.

The term "expressing" as used herein refers to the production of an ALP polypeptide from a nucleic acid vector containing an ALP gene within a cell. The nucleic acid vector is transfected into cells using well known techniques in the art as described herein.

The term "adding" as used herein refers to administering a solution comprising a compound to the medium bathing cells. The solution comprising the compound can also comprise an agent, such as dimethyl sulfoxide, which facilitates the uptake of the compound into the cells.

The term "monitoring" refers to observing the effect of adding the compound to the cells of the method. The effect can be manifested in a change in cell phenotype, cell proliferation, protein kinase catalytic activity, or in the interaction between a protein kinase and a natural binding partner.

The term "cell phenotype" refers to the outward appearance of a cell or tissue or the function of the cell or tissue. Examples of cell or tissue phenotype are cell size (reduction or enlargement), cell proliferation (increased or decreased numbers of cells), cell differentiation (a change or absence of a change in cell shape), cell survival, apoptosis (cell death), or the utilization of a metabolic nutrient (e.g., glucose uptake). Change or the absence of change in cell phenotype is readily measured by techniques known in the art.

The term "cell proliferation" refers to the rate at which a group of cells divides. The number of cells growing in a vessel can be quantitated by a person skilled in the art when that person visually counts the number of cells in a defined area using a common light microscope. Alternatively, cell proliferation rates can be quantitated by laboratory apparatae that optically measure the density of cells in an appropriate medium.

The method can utilize any of the molecules disclosed in the invention. These molecules include nucleic acid molecules encoding ALP polypeptides, nucleic acid vectors, recombinant cells, polypeptides, or antibodies of the invention.

In a preferred embodiment, the invention provides a method for treating or preventing an abnormal condition by administering a compound which is a modular of ALP function in vitro. The abnormal condition preferably involves abnormality in ALP signal transduction pathway, and most preferably is cancer. Such compounds preferably show positive results in one or more in vitro assays for an activity corresponding to treatment of the disease or disorder in question (such as the assays described in Example 6 below). Examples of substances that can be screened for favorable activity are provided in section XII below.

The summary of the invention described above is non-limiting and other features and advantages of the invention will be apparent from the following detailed description, and from the claims.

DETAILED DESCRIPTION OF THE INVENTION

The present invention relates to the isolation and characterization of a new protein which we have called ALP, nucleotide sequences encoding ALP, various products and assay methods that can be used to identify compounds useful for the diagnosis and treatment of various ALP related diseases and conditions, for example cancer. Polypeptides derived from ALP and nucleic acids encoding such polypeptides may be produced using well known and standard synthesis techniques when given the sequences presented herein.

ALP is a tyrosine phosphatase with an apparent molecular weight of approximately 160–200 kDa. Primary sequence analysis shows that ALP is comprised of three domains: a domain at the N-terminus that is rich in proline residues (30.6%) and contains several tyrosines that may be phosphorylated, a catalytic domain, and a C-terminal domain containing region rich in prolines and serines (45.6%) that resenbling a PEST motif (Rogers, et al; *Science* 234:364, 1986). These proline rich regions may be protein:protein interaction sites as SH3 domains have been shown to bind to proline rich regions (Morton and Campbell, *Curr. Biol.* 4:614, 1994; Ren, et al; *Science* 259:1157, 1993). The lack of a hydrophobic stretch of amino acids generally characterized as a transmembrane region indicates that ALP is a non-receptor tyrosine phosphatase.

The full-length ALP was originally isolated from a human brain cancer cell line. Subsequent expression analysis of both normal tissues and cancer cell lines, shown in detail below, revealed that ALP has low expression in normal cells but is significantly overexpressed in a number of tumors. This suggests that ALP plays an important role in the growth and persistance of these cancers.

The polypeptide and nucleotide sequences of the invention can be used, therefore, to identify modulators of cell growth and survival which are useful in developing therapeutics for various cell proliferative disorders and conditions, and in particular cancers related to inappropriate ALP activity. Assays to identify compounds that act intracellularly to enhance or inhibit ALP activity can be developed by creating genetically engineered cell lines that express ALP nucleotide sequences, as is more fully discussed below.

I. Nucleic Acids Encoding ALP Polypeptides

A first aspect of the invention features nucleic acid sequences encoding an ALP polypeptide. Included within the scope of this invention are the functional equivalents of the herein-described isolated nucleic acid molecules. Functional equivalents or derivatives can be obtained in several ways. The degeneracy of the genetic code permits substitution of certain codons by other codons which specify the same amino acid and hence would give rise to the same protein. The nucleic acid sequence can vary substantially since, with the exception of methionine and tryptophan, the known amino acids can be coded for by more than one codon. Thus, portions or all of the ALP gene could be synthesized to give a nucleic acid sequence significantly different from that shown in SEQ ID NO:1. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of the nucleic acid formula shown in SEQ ID NO:1 or a derivative thereof. Any nucleotide or polynucleotide may be used in this regard, provided that its addition, deletion or substitution does not alter the amino acid sequence of SEQ ID NO:2 which is encoded by the nucleotide sequence. For example, the present invention is intended to include any nucleic acid sequence resulting from the addition of ATG as an initiation codon at the 5'-end of the ALP nucleic acid sequence or its functional derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the ALP genes and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

Functional equivalents or derivatives of ALP can also be obtained using nucleic acid molecules encoding one or more functional domains of the ALP polypeptide. For example, the N-terminal proline-rich domain of ALP functions as a SH3 binding domain and a nucleic acid sequence encoding the N-terminal proline-rich domain alone or linked to other heterologous nucleic acid sequences can be considered a functional derivative of ALP. Other functional domains of ALP include, but are not limited to, the proline-rich region within the N-terminal proline-rich domain, the C-terminal proline/serine-rich domain, the proline/serine-rich region within the C-terminal proline/serin-rich domain, and the catalytic domain. Nucleic acid sequences encoding these domains are shown in SEQ ID NO:1 as follows: N-terminal domain 313–2883; proline-rich region 1369–2643; catalytic domain approximately 2884–3600, C-terminal proline/serine-rich domain 3601–4134, proline/serine-rich region 3613–4456.

II. A Nucleic Acid Probe for the Detection of ALP

A nucleic acid probe of the present invention may be used to probe an appropriate chromosomal or cDNA library by usual hybridization methods to obtain another nucleic acid molecule of the present invention. A chromosomal DNA or cDNA library may be prepared from appropriate cells according to recognized methods in the art (e.g. "Molecular Cloning: A Laboratory Manual", second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to PCR Protocols, "PCR Protocols, A Guide to Methods and Applications", edited by Innis et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (e.g. "Molecular Cloning: A Laboratory Manual", second edition, edited by Sambrook, Fritsch, & Maniatis, Cold Spring Harbor Laboratory, 1989). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA as well as DNA probes and nucleic acids modified in the sugar, phosphate or even the base portion as long as the probe still retains the ability to specifically hybridize under conditions as disclosed herein. Such probes are generated using techniques known in the art. The nucleic acid probe may be immobilized on a solid support. Examples of such solid supports include, but are not limited to, plastics such as polycarbonate, complex carbohydrates such as agarose and sepharose, acrylic resins, such as polyacrylamide and latex beads, and nitrocellulose. Techniques for coupling nucleic acid probes to such solid supports are well known in the art.

The test samples suitable for nucleic acid probing methods of the present invention include, for example, cells cr nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

III. A Probe Based Method And Kit For Detecting ALP

One method of detecting the presence of ALP in a sample comprises (a) contacting the sample with the above-described nucleic acid probe, under conditions such that hybridization occurs, and (b) detecting the presence of the probe bound to a nucleic acid molecule in the sample. One skilled in the art would select the nucleic acid probe according to techniques known in the art as described above. Samples to be tested include but should not be limited to RNA samples of human tissue.

A kit for detecting the presence of ALP in a sample comprises at least one container having disposed therein an above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymaticly labeled probes (horseradish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art.

IV. DNA Constructs Comprising an ALP Nucleic Acid Molecule and Cells Containing These Constructs The present invention also relates to a recombinant DNA molecule comprising, 5' to 3', a promoter effective to initiate transcription in a host cell and one of above-described nucleic acid molecules. In addition, the present invention relates to a recombinant DNA molecule comprising a vector and a nucleic acid molecule described herein. The present invention also relates to a nucleic acid molecule comprising a transcriptional region functional in a cell, a sequence complimentary to an RNA sequence encoding an amino acid sequence corresponding to an ALP polypeptide or functional derivative, and a transcriptional termination region functional in said cell. The above-described molecules may be isolated and/or purified DNA molecules.

The present invention also relates to a cell or organism that contains an ALP nucleic acid molecule as described herein and thereby is capable of expressing a peptide. The polypeptide may be purified from cells which have been altered to express the polypeptide. A cell is said to be "altered to express a desired polypeptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but will in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an ALP gene may be obtained by the above-described cloning methods. This region may be retained for its transcriptional termination regulatory sequences, such as termination and polyadenylation. Thus, by retaining the 3'-region naturally contiguous to the DNA sequence encoding an ALP gene, the transcriptional termination signals may be provided. Where the transcriptional termination signals are not satisfactorily functional in the expression host cell, then a 3' region functional in the host cell may be substituted.

Two DNA sequences (such as a promoter region sequence and an ALP sequence) are said to be operably linked if the nature of the linkage between the two DNA sequences does not (1) result in the introduction of a frame-shift mutation, (2) interfere with the ability of the promoter region sequence to direct the transcription of the second sequence, for example an ALP gene sequence, or (3) interfere with the ability of the second sequence to be transcribed by the promoter region sequence. Thus, a promoter region would be operably linked to a DNA sequence if the promoter were capable of effecting transcription of that DNA sequence. Thus transcriptional and translational signals recognized by an appropriate host are necessary to express an ALP gene.

The present invention encompasses the expression of an ALP gene (or a functional derivative thereof) in either prokaryotic or eukaryotic cells. Prokaryotic hosts are, generally, very efficient and convenient for the production of recombinant proteins and are, therefore, one type of preferred expression system for an ALP gene. Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include λgt10, λgt11 and the like; and suitable virus vectors may include pMAM-neo, pKRC and the like. Preferably, the selected vector of the present invention has the capacity to replicate in the selected host cell.

Recognized prokaryotic hosts include bacteria such as *E. coli* and those from genera such as Bacillus, Streptomyces, Pseudomonas, Salmonella, Serratia, and the like. However, under such conditions, the polypeptide will not be glycosylated. The prokaryotic host must be compatible with the replicon and control sequences in the expression plasmid.

To express ALP (or a functional derivative thereof) in a prokaryotic cell, it is necessary to operably link an ALP sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of constitutive promoters include the int promoter of bacteriophage 1, the bla promoter of the b-lactamase gene sequence of pBR322, and the CAT promoter of the chloramphenicol acetyl transferase gene sequence of pPR325, and the like. Examples of inducible prokaryotic promoters include the major right and left promoters of bacteriophage 1 ($P_L$ and $P_R$), the trp, recA, lacZ, lacI, and gal promoters of *E. coli*, the a-amylase (Ulmanen et al., *J. Bacteriol.* 162:176–182, 1985) and the sigma-28-specific promoters of *B. subtilis* (Gilman et al., *Gene Sequence* 32:11–20(1984)), the promoters of the bacteriophages of Bacillus (Gryczan, In: The Molecular Biology of the Bacilli, Academic Press, Inc., N.Y. (198.2)), and Streptomyces promoters (Ward et al., *Mol. Gen. Genet.* 203:468–478, 1986). Prokaryotic promoters are reviewed by Glick (*J. Ind. Microbiot.* 1:277–282, 1987); Cenatiempo (*Biochimie* 68:505–516, 1986); and Gottesman (*Ann. Rev. Genet.* 18:415–442, 1984).

Proper expression in a prokaryotic cell also requires the presence of a ribosome binding site upstream of the gene sequence-encoding sequence. Such ribosome binding sites are disclosed, for example, by Gold et at. (*Ann. Rev. Microbiol.* 35:365–404, 1981). The selection of control sequences, expression vectors, transformation methods, and the like, are dependent on the type of host cell used to express the gene.

As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the ALP peptide of interest. Suitable hosts may often include eukaryotic cells. Preferred eukaryotic hosts include, for example, yeast, fungi, insect cells, and mammalian cells, either in vivo or in tissue culture. Mammalian cells which may be useful as hosts include HeLa cells, cells of fibroblast origin such as VERO, 3T3 or CHO-K1, or cells of lymphoid origin (such as 32D cells) and their derivatives. Preferred mammalian host cells include SP2/0 and J558L, as well as neuroblastoma cell lines such as IMR 332 and PC12 which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the *Drosophila larvae*. Using insect cells as hosts, the Drosophila alcohol dehydrogenase promoter can be used. Rubin, *Science* 240:1453–1459, 1988). Alternatively, baculovirus vectors can be engineered to express large amounts of ALP in insects cells (Jasny, *Science* 238:1653, 1987); Miller et al., In: Genetic Engineering (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., prepeptides). For a mammalian host, several possible vector systems are available for the expression of ALP.

A particularly preferred yeast expression system is that utilizing Schizosaccharmocyces pombe. This system is useful for studying the activity of members of the Src family (Superti-Furga, et al, *EMBO J.* 12:2625, 1993) and other non-receptor tyrosine kinases, the function of which is often regulated by the activity of tyrosine phosphatases.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of ALP in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288, 1982); the TK promoter of Herpes virus (McKnight, *Cell* 31:355–365, 1982); the SV40 early promoter (Benoist et al., *Nature* (London) 290:304–310, 1981); the yeast gal4 gene sequence promoter (Johnston et al., *Proc. Natl. Acad. Sci. USA* 79:6971–6975, 1982); Silver et al., *Proc. Natl. Acad. Sci. USA* 81:5951–5955, 1984).

Translation of eukaryotic mRNA is initiated at the codon which encodes the first methionine. For this reason, it is preferable to ensure that the linkage between a eukaryotic promoter and a DNA sequence which encodes ALP (or a functional derivative thereof) does not contain any intervening codons which are capable of encoding a methionine (i.e., AUG). The presence of such codons results either in the formation of a fusion protein (if the AUG codon is in the same reading frame as the ALP coding sequence) or a frame-shift mutation (if the AUG codon is not in the same reading frame as the ALP coding sequence).

An ALP nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule (a plasmid). Since such molecules are incapable of autonomous replication, the expression of the gene may occur through the transient expression of the introduced sequence. Alternatively, permanent or stable expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, *Mol. Cell. Bio.* 3:280, 1983.

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coil* (such as, for example, pBR322, ColEl, pSC101, pACYC 184, pVX. Such plasmids are, for example, disclosed by Sambrook (cf. "Molecular Cloning: A Laboratory Manual", second edition, edited by Sambrook, Fritsch, & Maniatis, Cold Spring Harbor Laboratory, (1989)). Bacillus plasmids include pC194, pC221, pT127, and the like. Such plasmids are disclosed by Gryczan (In: The Molecular Biology of the Bacilli, Academic Press, NY (1982), pp. 307–329). Suitable Streptomyces plasmids include p1J101 (Kendall et al., *J. Bacteriol.* 169:4177–4183,1987), and streptomyces bacteriophages such as fC31 (Chater et al., In: Sixth International Symposium on Actinomycetales Biology, Akademiai Kaido, Budapest, Hungary (1986), pp. 45–54). Pseudomonas plasmids are reviewed by John et al. (*Rev. Infect. Dis.* 8:693–704, 1986), and Izaki (Jpn. *J. Bacteriol.* 33:729–742, 1978).

Preferred eukaryotic plasmids include, for example, BPV, vaccinia, SV40, 2-micron circle, and the like, or their derivatives. Such plasmids are well known in the art (Botstein et al., Miami Wntr. Symp. 19:265–274, 1982); Broach, In: "The Molecular Biology of the Yeast Saccharomyces: Life Cycle and Inheritance", Cold Spring Harbor Laboratory, Cold Spring Harbor, N.Y., p. 445–470 (1981); Broach, *Cell* 28:203–204, 1982); Bollon et at., *J. Clin. Hematol. Oncol.* 10:39–48, 1980); Maniatis, In: *Cell Biology: A Comprehensive Treatise*, Vol. 3, *Gene Sequence Expression*, Academic Press, N.Y., pp. 563–608 (1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of ALP or fragments or functional derivatives thereof. This can take place in the transformed cells as such, or following the induction of these cells to differentiate (for example, by administration of bromodeoxyuracil to neuroblastoma cells or the like). A variety of incubation conditions for the transformed cells can be used to foster expression of the polypeptides of the peptide of the present invention. The most preferred conditions are those which mimic physiological conditions.

V. ALP Polypeptides

Also a feature of the invention are ALP polypeptides. A variety of methodologies known in the art can be utilized to obtain the polypeptides of the present invention. They may be purified from tissues or cells which naturally produce them. Alternatively, the above-described isolated nucleic acid sequences can be used to express an ALP protein recombinantly.

Any eukaryotic organism can be used as a source for the polypeptide of the invention, as long as the source organism naturally contains such a polypeptide. As used herein, "source organism" refers to the original organism from which the amino acid sequence is derived, regardless of the organism the protein is expressed in and ultimately isolated from.

One skilled in the art can readily follow known methods for isolating proteins in order to obtain the peptide free of natural contaminants. These include, but are not limited to: size-exclusion chromatography, HPLC, ion-exchange chromatography, and immuno-affinity chromatography.

An ALP protein, like all proteins, is comprised of distinct functional units or domains. In eukaryotes, proteins sorted through the so-called vesicular pathway (bulk flow) usually have a signal sequence (also called a leader peptide) in the N-terminus, which is cleaved off after the translocation through the ER (endoplasmic reticulum) membrane. Some N-terminal signal sequences are not cleaved off, remaining as transmembrane segments, but it does not mean these proteins are retained in the ER; they can be further sorted and included in vesicles. Non-receptor proteins generally function to transmit signals within the cell, either by providing sites for protein:protein interactions or by having some catalytic activity (contained within a catalytic domain), often both. Methods of predicting the existence of these various domains are well known in the art. Protein-:protein interaction domains can be identified by comparison to other proteins. The SH2 domain, for example is a protein domain of about 100 amino acids first identified as a conserved sequence region between the proteins Src and Fps (Sadowski; et al, *Mol. Cell. Bio.* 6:4396, 1986). Similar sequences were later found in many other intracellular signal-transducing proteins. SH2 domains function as regulatory modules of intracellular signalling cascades by interacting with high affinity to phosphotyrosine-containing proteins in a sequence specific and strictly phosphorylation-dependent manner (Mayer and Baltimore, Trends *Cell. Biol.* 3:8, 1993). Kinase or phosphatase catalytic domains can be identified by comparison to other known catalytic domains with kinase phosphatase activity. See, for example Hanks and Hunter, *FASEB J.* 9:576–595, 1995.

Primary sequence analysis of the ALP amino acid sequence (shown in SEQ ID NO: 2) reveals that it does not contain a signal sequence or transmembrane domain and is, therefore, an intracellular protein. Comparison to known protein sequences revels that ALP is comprised of several unique domains. These include a 857 amino acid N-terminal proline-rich domain (shown from amino acid number 1–857 of SEQ ID NO: 2) within which is a proline-rich region (amino acid number 353–777 of SEQ ID NO:2), a 238 amino acid catalytic domain (shown from amino acid number 858–1096 of SEQ ID NO: 2), and a 177 amino acid C-terminal proline/serine-rich domain (shown from amino acid number 1097–1274 of SEQ ID NO:2) within which is a proline/serine-rich region (amino acid number 1101–1214 of SEQ ID NO:2).

These ALP domains have a variety of uses. An example of such a use is to make a polypeptide consisting of the ALP catalytic domain and a heterologous protein such as glutathione S-transferase (GST). Such a polypeptide can be used in a biochemical assay for ALP catalytic activity useful for studying ALP substrate specificity or for identifying substances that can modulate ALP catalytic activity. Alternatively, one skilled in the art could create an ALP polypetide lacking at least one of the three major domains. Such a polypeptide, when expressed in a cell, is able to form complexes with the natuaral binding partner(s) of ALP but unable to transmit any signal further downstream into the cell, ie. it would be signaling incompetent and thus would be useful for studying the biological relevance of ALP activity. (See, as an example, Gishizky, et al; *PNAS*: 10889, 1995).

VI. An Antibody Having Binding Affinity To An ALP Polypeptide And A Hybridoma Containing the Antibody The present invention also relates to an antibody having specific binding affinity to an ALP polypeptide. The polypeptide may have the amino acid sequence set forth in SEQ ID NO:2, or a be fragment thereof, or at least 6 contiguous amino acids thereof. Such an antibody may be identified by comparing its binding affinity to an ALP polypeptide with its binding affinity to another polypeptide. Those which bind selectively to ALP would be chosen for use in methods requiring a distinction between ALP and other polypeptides. Such methods could include, but should not be limited to, the analysis of altered ALP expression in tissue containing other polypeptides and assay systems using whole cells.

An ALP peptide of the present invention can be used to produce antibodies or hybridomas. One skilled in the art will recognize that if an antibody is desired, such a peptide would be generated as described herein and used as an immunogen. A preferred ALP peptide in this respect is the sequence from amino acids 1 to 352 of SEQ ID NO:2. The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting. The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands, 1984; St. Groth et al., *J. Immunol. Methods* 35:1–21, 1980). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz, et al., *Exp. Cell Res*. 175:109–124, 1988). Hybridomas secreting the desired antibodies are cloned and the class and subclass is determined using procedures known in the art (Campbell, "Monoclonal Antibody Technology: Laboratory Techniques in Biochemistry and Molecular Biology", supra, 1984).

For polyclonal antibodies, antibody containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Stemberger, et al., *J. Histochem. Cytochem*. 18:315, 1970; Bayer, et at., *Meth. Enzym*. 62:308, 1979; Engval, et al., *Immunot*. 109:129, 1972; Godding, *J. Immunol. Meth*. 13:215, 1976). The labeled antibodies of the present invention can be used for in vitro, in vivo, and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10, 1986; Jacoby et al., *Meth. Enzym*. 34, Academic Press, N.Y., 1974). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In Synthetic Peptides, A User's Guide, W.H. Freeman, N.Y., pp. 289–307 (1992), and Kaspczak et al., *Biochemistry* 28:9230–8(1989).

VII. An Antibody Based Method And Kit For Detecting ALP

The present invention encompasses a method of detecting an ALP polypeptide in a sample, comprising incubating a test sample with one or more of the antibodies of the present invention and determining whether the antibody binds to the test sample. The method can include the steps of, for example: (a) contacting the sample with an above-described antibody, under conditions such that immunocomplexes form, and (b) detecting the presence of said antibody bound to the polypeptide. Altered levels, either an increase or decrease, of ALP in a sample as compared to normal levels may indicate disease.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques" Elsevier Science Publishers, Amsterdam, The Netherlands (1986); Bullock et al., "Techniques in Immunocytochemistry," Academic Press, Orlando, Fla. Vol. 1(1982), Vol. 2 (1983), Vol. 3 (1985); Tijssen, "Practice and Theory of Enzyme Immunoassays: Laboratory Techniques in Biochemistry and Molecular Biology," Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily adapted in order to obtain a sample which is compatable with the system utilized.

A kit contains all the necessary reagents to carry out the previously described methods of detection. The kit may comprise: (i) a first container containing an above-described antibody, and (ii) second container containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits. One skilled in the art will recognize that the antibodies described in the present invention can readily be incorporated into one of the established kit formats which are well known in the art.

VIII. Isolation of Natural Binding Partners of ALP

The present invention also relates to methods of detecting natural binding partners capable of binding to an ALP polypeptide. A natural binding partner of ALP may be, for example, an SH3 domain containing protein which can interact with an ALP proline-rich domain as part of a signaling cascade. The binding parter(s) may be present within a complex mixture, for example, serum, body fluids, or cell extracts.

In general methods for identifying natural binding partners comprise incubating a substance with ALP and detecting the presence of a substance bound to ALP. Preferred methods include the two-hybrid system of Fields and Song (supra) and co-immunoprecipitation wherein an ALP polypeptide is allowed to bind to a natural binding partner, then the polypeptide complex is immunoprecipitated using ALP-specific antibodies. The natural binding partner can then be isolated and identified by techniques well known in the art.

IX. Identification of and Uses for Substances Capable of Modulating ALP Activity The present invention also relates to a method of detecting a substance capable of modulating ALP activity. Such substances can either enhance activity (agonists) or inhibit activity (antagonists). Agonists and antagonists can be peptides, antibodies, products from natural sources such as fungal or plant extracts or small molecular weight organic compounds. In general, small molecular weight organic compounds are preferred. Examples of classes of compounds that can be tested for ALP modulating activity are, for example but not limited to, thiazoles (see for example co-pending U.S. applications Ser. No. 60/033,522, filed Dec. 19, 1996; 08/660,900, filed Jun. 7, 1996), and naphthopyrones (U.S. Pat. No. 5,602,171, issued Feb. 11, 1997).

In general the method comprises incubating cells that produce ALP in the presence of a test substance and detecting changes in the level of ALP activity or ALP binding partner activity. A change in activity may be manifested by increased or decreased phosphorylation of an ALP polypeptide, increased or decreased phosphorylation of an ALP substrate, increased or decreased binding to an ALP natural binding partner or increased or decreased biological response in cells. A method for detecting modulation of ALP activity using the phosphorylation of an artificial substrate is shown in the examples below. Biological responses can include, for example, proliferation, differentiation, survival, or motility. The substance thus identified would produce a change in activity indicative of the agonist or antagonist nature of the substance. Once the substance is identified it can be isolated using techniques well known in the art, if not already available in a purified form.

The present invention also encompasses a method of agonizing (stimulating) or antagonizing ALP associated activity in a mammal comprising administering to said mammal an agonist or antagonist to ALP in an amount sufficient to effect said agonism or antagonism. Also encompassed in the present application is a method of treating diseases in a mammal with an agonist or antagonist of ALP-related activity comprising administering the agonist or antagonist to a mammal in an amount sufficient to agonize or antagonize ALP associated function(s). The particular compound can be administered to a patient either by itself or in a pharmaceutical composition where it is mixed with suitable carriers or excipient(s). In treating a patient, a therapeutically effective dose of the compound is administered. A therapeutically effective dose referes to that amount of the compound that results in amelioration of symptioms or a prolongation of survival in a patient.

Toxicity and therapeutic efficacy of such compounds can be determined by standard pharmaceutical procedures in cell cultures cr experimental animals. Cell cluture assays and animal studies can be used for determining the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Compounds which exhibit large therapeutic indices are preferred. The data obtained from these cell culture assays and animal studies can be used in formulating a range of dosages for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays by determining an $IC_{50}$ (i.e., the concentration of the test compound which achieves a half-maximal disruption of the protein complex, or a half-maximal inhibition of the cellular level and/or activity of a cellular component, ex. ALP). A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact formulation, route of administration and dosage can be chosen by the individual physician in view of the patient's condition. (See e.g. Fingl et al., 1975, in "The Pharmacological Basis of Therapeutics", Ch. 1, p. 1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in "Remington's Pharmaceutical Sciences," 1990, 18th ed., Mack Publishing Co., Easton, Pa. Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated. Particlar formulations suitable for parenteral administration of hydrophobic compounds can be found in U.S. Pat. No. 5,610,173, issued Mar. 11, 1997 and U.S. Provisional Application Ser. No. 60/039,870, filed Mar. 05, 1997, both of which are incorporated by reference herein in their entirety.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Small organic molecules may be directly administered intracellularly due to their hydrophobicity.

Pharmaceutical compositions suitable for use in the present invention include compositions wherein the active ingredients are contained in an amount effective to achieve its intended purpose. Determination of an effective amount is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose,sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

X. Transgenic Animals

Also contemplated by the invention are transgenic animals useful for the study of ALP activity in complex in vivo systems. A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. The transgenic DNA may encode for a human ALP polypeptide. Native expression in an animal may alternatively be reduced by providing an amount of antisense RNA or DNA effective to reduce expression of the target gene.

A variety of methods are available for the production of transgenic animals associated with this invention. DNA sequences encoding ALP can be injected into the pronucleus of a fertilized egg before fusion of the male and female pronuclei, or injected into the nucleus of an embryonic cell (e.g., the nucleus of a two cell embryo) following the initiation of cell division (Brinster, et al., Proc. Nat. Acad. Sci. USA 82: 4438, 1985). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan, et al., supra). Microinjection procedures for fish, amphibian eggs and birds are detailed in Houdebine and Chourrout, Experientia 47: 897–905, 1991). Other procedures for introduction of DNA into tissues of animals are described in U.S. Pat. No. , 4,945,050 (Sandford et al., Jul. 30, 1990).

By way of example only, to prepare a transgenic mouse, female mice are induced to superovulate. After being allowed to mate, the females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer, et al., Cell 63:1099–1112, 1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. (See, for example, Teratocarcinomas and Embryonic Stem Cells, A Practical Approach, E. J. Robertson, ed., IRL Press, 1987). In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra). DNA molecules introduced into ES cells can also be integrated into the chromosome through the process of homologous recombination. (Capecchi, Science 244:1288, 1989). Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al., (Nature 338:153, 1989), the teachings of which are incorporated by reference herein. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others. (See Houdebine and Chourrout, supra; Pursel, et al., Science 244:1281, 1989; Simms, et al., Bio/Technology 6:179, 1988).

Thus, the invention provides transgenic, nonhuman mammals containing a transgene encoding an ALP polypeptide or a gene effecting the expression of an ALP polypeptide. Such transgenic nonhuman mammals are particularly useful as an in vivo test system for studying the effects of introducing an ALP polypeptide, regulating the expression of an ALP polypeptide (i.e., through the introduction of additional genes, antisense nucleic acids, or ribozymes).

XI. Gene Therapy

ALP nucleic acid sequences, both mutated and non-mutated, will also be useful in gene therapy (reviewed in Miller, Nature 357:455–460, (1992). Miller states that advances have resulted in practical approaches to human gene therapy that have demonstrated positive initial results. The basic science of gene therapy is described in Mulligan, Science 260:926, 1993. As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In one preferred embodiment, an expression vector containing an ALP coding sequence or an ALP mutant coding sequence as described above is inserted into cells, the cells are grown in vitro and then infused in large numbers into patients. In another preferred embodiment, a DNA segment containing a promoter of choice (for example a strong promoter) is transferred into cells containing an endogenous ALP in such a manner that the promoter segment enhances expression of the endogenous ALP gene (for example, the promoter segment is transferred to the cell such that it becomes directly linked to the endogenous ALP gene).

The gene therapy may involve the use of an adenovirus containing ALP cDNA targeted to an appropriate cell type, systemic ALP increase by implantation of engineered cells, injection with ALP virus, or injection of naked ALP DNA into appropriate cells or tissues, for example neurons.

Expression vectors derived from viruses such as retroviruses, vaccinia virus, adenovirus, adeno-associated virus, herpes viruses, other RNA viruses, or bovine papilloma virus, may be used for delivery of nucleotide sequences (e.g., cDNA) encoding recombinant ALP protein into the targeted cell population (e.g., tumor cells or neurons). Methods which are well known to those skilled in the art can be used to construct recombinant viral vectors containing coding sequences. See, for example, the techniques described in Maniatis et al., Molecular Cloning: A Laboratory Manual, Cold Spring Harbor Laboratory, N.Y. (1989), and in Ausubel et al., Current Protocols in Molecular Biology, Greene Publishing Associates and Wiley Interscience, N.Y. (1989). Alternatively, recombinant nucleic acid molecules encoding protein sequences can be used as naked DNA or in reconstituted system, e.g., liposomes or other lipid systems for delivery to target cells (See e.g., Felgner et al., Nature 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. (Capecchi M R, Cell 22:479–88, 1980). Once recombinant genes are introduced into a cell, they can be recognized by the cells normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen C. and Okayama H, Mol. Cell Biol. 7:2745–52, 1987); electroporation, wherein cells are exposed to large voltage pulses to introduce holes into the membrane (Chu G., et al., Nucleic Acids Res., 15:1311–26, 1987); lipofection/liposome fusion, wherein DNA is packaged into lipophilic vesicles which fuse with a target cell (Felgner P L., et al., Proc. Natl. Acad. Sci. USA. 84:7413–7, 1987)); and particle bombardment using DNA bound to small projectiles (Yang N S. et al., Proc. Natl. Acad. Sci. 87:9568–72, 1990). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel D T.

As used herein "gene transfer" means the process of introducing a foreign nucleic acid molecule into a cell. Gene transfer is commonly performed to enable the expression of a particular product encoded by the gene. The product may include a protein, polypeptide, antisense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

In another preferred embodiment, a vector having nucleic acid sequences encoding an ALP is provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

XII. Compounds that Modulate the Function of ALP Proteins

In an effort to discover novel treatments for diseases, biomedical researchers and chemists have designed, synthesized, and tested molecules that inhibit the function of protein kinases. Some small organic molecules form a class of compounds that modulate the function of protein kinases. Examples of molecules that have been reported to inhibit the function of protein kinases include, but are not limited to, bis monocyclic, bicyclic or heterocyclic aryl compounds (PCT WO 92/20642, published Nov. 26, 1992 by Maguire et al.), vinylene-azaindole derivatives (PCT WO 94/14808, published Jul. 7, 1994 by Ballinari et al.), 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT WO 94/03427, published Feb. 17, 1994 by Denny et al.), tricyclic polyhydroxylic compounds (PCT WO 92/21660, published Dec. 10, 1992 by Dow), and benzylphosphonic acid compounds (PCT WO 91/15495, published Oct. 17, 1991 by Dow et al). The compounds that can traverse cell membranes and are resistant to acid hydrolysis are potentially advantageous therapeutics as they can become highly bioavailable after being administered orally to patients. However, many of these protein kinase inhibitors only weakly inhibit the function of protein kinases. In addition, many inhibit a variety of protein kinases and will therefore cause multiple side-effects as therapeutics for diseases.

Some indolinone compounds, however, form classes of acid resistant and membrane permeable organic molecules. WO 96/22976, published Aug. 1, 1996 by Ballinari et al. describes hydrosoluble indolinone compounds that harbor tetralin, naphthalene, quinoline, and indole substituents fused to the oxindole ring. These bicyclic substituents are in turn substituted with polar moieties including hydroxylated alkyl, phosphate, and ether moieties. U.S. patent application Ser. Nos. 08/702,232, filed Aug. 23, 1996, entitled "Indolinone Combinatorial Libraries and Related Products and Methods for the Treatment of Disease" by Tang et al. (Lyon & Lyon Docket No. 221/187) and 08/485,323, filed Jun. 7, 1995, entitled "Benzylidene-Z-Indoline Compounds for the Treatment of Disease" by Tang et al. (Lyon & Lyon Docket No. 223/298) and International Patent Publication WO 96/22976, published Aug. 1, 1996 by Ballinari et al., all of which are incorporated herein by reference in their entirety, including any drawings, describe indolinone chemical libraries of indolinone compounds harboring other bicyclic moieties as well as monocyclic moieties fused to the oxindole ring. applications Ser. No. 08/702,232, filed Aug. 23, 1996, entitled "Indolinone Combinatorial Libraries and Related Products and Methods for the Treatment of Disease" by Tang et al. (Lyon & Lyon Docket No. 221/187), Ser. No. 08/485,323, filed Jun. 7, 1995, entitled "Benzylidene-Z-Indoline Compounds for the Treatment of Disease" by Tang et al. (Lyon & Lyon Docket No. 223/298), and WO 96/22976, published Aug. 1, 1996 by Ballinari et al. teach methods of indolinone synthesis, methods of testing the biological activity of indolinone compounds in cells, and inhibition patterns of indolinone derivatives.

Other examples of substances capable of modulating ALP activity include, but are not limited to, tyrphostins, quinazolines, quinoxolines, and quinolines.

The quinazolines, tyrphostins, quinolines, and quinoxolines referred to above include well known compounds such as those described in the literature. For example, representative publications describing quinazoline include Barker et al., EPO Publication No. 0 520 722 A1; Jones et al., U.S. Pat. No. 4,447,608; Kabbe et al., U.S. Pat. No. 4,757,072; Kaul and Vougioukas, U.S. Pat. No. 5, 316,553; Kreighbaum and Comer, U.S. Pat. No. 4,343,940; Pegg and Wardleworth, EPO Publication No. 0 562 734 A1; Barker et al., *Proc. of Am. Assoc. for Cancer Research* 32:327 (1991); Bertino, J. R., *Cancer Research* 3:293–304 (1979); Bertino, J. R., *Cancer Research* 9(2 part 1):293–304 (1979); Curtin et al., *Br. J. Cancer* 53:361–368 (1986); Fernandes et al., *Cancer Research* 43:1117–1123 (1983); Ferris et al. *J. Org. Chem.* 44(2):173–178; Fry et al., *Science* 265:1093–1095 (1994); Jackman et al., *Cancer Research* 51:5579–5586 (1981); Jones et al. *J. Med. Chem.* 29(6):1114–1118; Lee and Skibo, *Biochemistry* 26(23):7355–7362 (1987); Lemus et al., *J. Org. Chem.* 54:3511–3518 (1989); Ley and Seng, *Synthesis* 1975:415–522 (1975); Maxwell et al., *Magnetic Resonance in Medicine* 17:189–196 (1991); Mini et al., *Cancer Research* 45:325–330 (1985); Phillips and Castle, *J. Heterocyclic Chem.* 17(19):1489–1596 (1980); Reece et al., *Cancer Research* 47(11):2996–2999 (1977); Sculier et al., *Cancer Immunol. and Immunother.* 23: A65 (1986); Sikora et al., *Cancer Letters* 23:289–295 (1984); Sikora et al., *Analytical Biochem.* 172:344–355 (1988); all of which are incorporated herein by reference in their entirety, including any drawings.

Quinoxaline is described in Kaul and Vougioukas, U.S. Pat. No. 5,316,553, incorporated herein by reference in its entirety, including any drawings.

Quinolines are described in Dolle et al., *J. Med. Chem.* 37:2627–2629 (1994); MaGuire, *J. Med. Chem.* 37:2129–2131 (1994); Burke et al., *J. Med. Chem.* 36:425–432 (1993); and Burke et al. *BioOrganic Med. Chem. Letters* 2:1771–1774 (1992), all of which are incorporated by reference in their entirety, including any drawings.

Tyrphostins are described in Allen et al., *Clin. Exp. Immunol.* 91:141–156 (1993); Anafi et al., *Blood* 82:12:3524–3529 (1993); Baker et al., *J. Cell Sci.* 102:543–555 (1992); Bilder et al., *Amer. Physiol. Soc. pp.* 6363–6143: C721–C730 (1991); Brunton et al., *Proceedings of Amer. Assoc. Cancer Rsch.* 33:558 (1992); Bryckaert et al., *Experimental Cell Research* 199:255–261 (1992); Dong et al., *J. Leukocyte Biology* 53:53–60 (1993); Dong et al., *J. Immunol.* 151(5):2717–2724 (1993); Gazit et al., *J. Med. Chem.* 32:2344–2352 (1989); Gazit et al., *J. Med. Chem.* 36:3556–3564 (1993); Kaur et al., *Anti-Cancer Drugs* 5:213–222 (1994); Kaur et al., King et al., *Biochem. J.* 275:413–418 (1991); Kuo et al., *Cancer Letters* 74:197–202 (1993); Levitzki, A., *The FASEB J.* 6:3275–3282 (1992); Lyall et al., *J. Biol. Chem.* 264:14503–14509 (1989); Peterson et al., *The Prostate* 22:335–345 (1993); Pillemer et al., *Int. J. Cancer* 50:80–85 (1992); Posner et al., *Molecular Pharmacology* 45:673–683 (1993); Rendu et al., *Biol. Pharmacology* 44(5):881–888 (1992); Sauro and Thomas, *Life Sciences* 53:371–376 (1993); Sauro and Thomas, *J. Pharm. and Experimental Therapeutics* 267(3):119–1125 (1993); Wolbring et al., *J. Biol. Chem.* 269(36):22470–22472 (1994); and Yoneda et al., *Cancer Research* 51:4430–4435 (1991); all of which are incorporated herein by reference in their entirety, including any drawings.

EXAMPLES

EXAMPLE 1

Isolation of cDNA Clones Encoding ALP

The example below describes the isolation and identification of a new PTP sequence from mouse tissues and the subsequent cloning of a full-length human ALP. Also described are probes useful for the detection of ALP in cells or tissues.

Materials and Methods:

Total RNAs were isolated using a commonly known guanidine salts/phenol extraction protocol from normal mouse fat and rat pituitary. Chomczynski & Sacchi, 1987, *Anal. Biochem.* 162: 156. These RNA extracts were used to generate single-stranded cDNA using the Superscript Preamplification System (GIBCO BRL, Gaithersburg, Md.; Gerard et al., 1989, *FOCUS* 11: 66) under conditions recommended by the manufacturer. a typical reaction used 10 $\mu$g total RNA with 1.5 $\mu$g oligo(dT)$_{12-18}$ in a reaction volume of 60 $\mu$L. The product was treated with RNaseH and diluted to 100 $\mu$L with $H_2O$. For subsequent PCR amplification, 1–4 $\mu$L of this sscDNA was used in each reaction.

Degenerate oligonucleotides were synthesized on an Applied Biosystems 394 DNA synthesizer using established phosphoramidite chemistry, precipitated with ethanol and used unpurified for PCR. The sequence of the degenerate oligonucleotide primers were as follows:

PTPDFW=5'-GAYTTYTGGVRNATGRTNTGGGA-3' (SEQ ID NO:3)
PTPHCSAG=5'-CGGCCSAYNCCNGCNSWRCARTG-3' (SEQ ID NO:4)
PTPYINA =5'-ATCCCCGGCTCTGAYTAYATHMAYGC-3' (SEQ ID NO:5)

These primers were derived from the peptide sequences DFWXMXW(E/D) (SEQ ID NO:6) (sense strand from PTP catalytic region) and HCXAGXG (SEQ ID NO:7)(antisense strand from PTP catalytic region), and IPGSDYI(N/H)A (SEQ ID NO:8) respectively. The standard UIPAC designations for degenerate residue designations are: N=A, C, G, or T; R=A or G; Y=C or T; V=A, C or G; W=C or T; S=C or G; M=A or C; and H=A, C or T.

PCR reactions were performed using degenerate primers applied to the single-stranded cDNA listed above. The primers were added at a final concentration of 5 µM each to a mixture containing 10 mM TrisHCl (pH8.3), 50 mM KCl, 1.5 mM $MgCl_2$, 200 mM each deoxynucleoside triphosphate, 0.001% gelatin, 1.5 U AmpliTaq DNA Polymerase (Perkin-Elmer/Cetus), and 1–4 µL cDNA. Following 3 min denaturation at 95° C., the cycling conditions were 94° C. for 30 s, 50° C. for 1 min, and 72° C. for 1 min 45 s for 35 cycles. PCR fragments migrating between 350–400 bp were isolated from 2% agarose gels using the GeneClean Kit (BiolOl), and T-A cloned into the PCRII vector (Invitrogen Corp. U.S.A.) according to the manufacturer's protocol.

Colonies were selected for mini plasmid DNA-preparations using Qiagen columns and the plasmid DNA was sequenced using cycle sequencing dye-terminator kit with AmpliTaq DNA Polymerase, FS (ABI, Foster City, Calif.). Sequencing reaction products were run on an ABI Prism 377 DNA Sequencer, and analyzed using the BLAST alignment algorithm. Altschul et al., *J. Mol. Biol.* 215: 403–410. A single clone encoding a novel PTP (S50–151), designated murine ALP, was isolated from murine adipose tissue using degenerate oligonucleotides PTPDFW (SEQ ID NO:3) and PTPHCSAG (SEQ ID NO:4), and a related rat ALP clone was isolated from rat pituitary using degenerate oligonucleotides PTPYINA (SEQ ID NO:5) and PTPHC-SAG (SEQ ID NO:4).

To isolate a full-length human ALP a human cDNA library was constructed in lambda ZapII (Stratagene, La Jolla, Calif.) from polyA+ RNA isolated from the human neuroblastoma cell line IMR32. The library was screened to isolate full-length transcripts encoding ALP. The murine ALP fragment was $^{32}$P-labeled by random priming and used as a hybridization probe at $2×10^6$ cpm/mL following standard techniques for library screening. Pre-hybridization (3 h) and hybridization (overnight) were conducted at 42° C. in 5×SSC, 5×Denhart's solution, 2.5% dextran sulfate, 50 mM $Na_2PO_4$/NaHPO$_4$ [pH 7.0], 50%; formamide with 100 mg/mL denatured salmon sperm DNA. Stringent washes were performed at 65° C. in 0.1×SSC with 0.1% SDS. Multiple clones were isolated and one 4.5 kb clone spanned the entire coding region of ALP. The final sequence was verified by sequencing of both strands using a cycle sequencing dye-terminator kit with AmpliTaq DNA Polymerase, FS (ABI, Foster City, Calif.). Sequencing reaction products were run on an ABI Prism 377 DNA Sequencer.

Results:

The 4,456 bp human ALP nucleotide sequence encodes a polypeptide of 1,274 amino acids. The amino acid sequence shows no signal sequence or a transmembrane domain and is therefore an intracellular protein. The N-terminal end extends from amino acids 1–857 and contains several putative tyrosine phosphorylation sites and a proline-rich region (30.6% prolines) from amino acids 353–777. This proline-rich region is distantly related to plant extensin proteins (30.2% amino acid identity with *Zea mays* extensin-like protein GB:Z34465 using Smith-Waterman alignment) and may represent a protein interaction domain as well as the site for interaction with proteins containg SH3 motifs. The C-terminal tail of ALP extends from amino acid 1097–1274 and contains a proline/serine rich region (45.6% serines plus prolines from amino acids 1101–1214) resembling a PEST motif. This region also could serve as a target for binding proteins via their SH3 motifs.

The catalytic domain extends from amino acids 858–1096 and shares 32–37% amino acid identity to PTPs from multiple subfamilies: TC-PTP (P17706: 37.1%) PTP-BAS (D21209: 32.9%), PTPα (M34668: 34.2%), PTPβ (P23467: 34.2%), PTPσ (A49104: 33.2%), PTP1B (P20417: 34.9%), suggesting that it represents a new family of PTPs. While all other cytoplasmic PTPs have their catalytic domain at either the N- or C-terminal portion of the protein, ALP has a central catalytic domain flanked by large N- and C-terminal domains. Its catalytic domain conserves most of the invariant residues present in other PTPs, but does has several atypical amino acids. In ALP, the amino acid sequence HCSAG (SEQ ID NO:6), is changed to HCSSG (amino acid positions 1029–1033) (SEQ ID NO:7). This motif is in the catalytic site of the crystal stucture of PTP1B and PTPa, and the Ala to Ser change may effect catalyitic activity or specificty. ALP also has a change from WPD to WPE (amino acids positions 993–995) in its predicted surface loop of the catalytic domain. In PTP1B this Aspartate participates in a salt bridge and falls into the catalytic site on binding to a specific peptide substrate. This Asp to Glu alteration is also present in three other mammalian PTPs (PTPD1, PCP2, PTPS31).

EXAMPLE 2

Expression of ALP

The example below shows the evaluation of ALP expression in normal human tissues and in a wide variety of cancers.

Materials and Methods:

Northern blots were prepared by running 20 µg total RNA per lane isolated from 60 different tumor cell lines (HOP-92, EKVX, NCI-H23, NCI-H226, NCI-H322M, NCI-H460, NCI-H522, A549, HOP-62, OVCAR-3, OVCAR-4, OVCAR-5, OVCAR-8, IGROV1, SK-OV-3, SNB-19, SNB-75, U251, SF-268, SF-295, SF-539, CCRF-CEM, K-562, MOLT-4, HL-60, RPMI 8226, SR, DU-145, PC-3, HT-29, HCC-2998, HCT-116, SW620, Colo 205, HTC15, KM-12, UO-31, SN12C, A498, CaKil, RXF-393, ACHN, 786-0, TK-10, LOX IMVI, Malme-3M, SK-MEL-2, SK-MEL-5, SK-MEL-28, UACC-62, UACC-257, M14, MCF-7, MCF-7/ADR RES, Hs578T, MDA-MB-231, MDA-MB-435, MDA-N, BT-549, T47D). (obtained from Nick Scuidero, National Cancer Institute, Developmental Therapeutics Program, Rockville, Md.). The total RNA samples were run on a denaturing formaldehyde 1% agarose gel and transferred onto a nitrocellulose membrane (BioRad, Calif.). Additional human normal tissue Northern blots containing 2 µg polyA+mRNA per lane from 16 different human normal tissues (thymus, lung, colon, testis, brain, heart, liver, pancreas, kidney, spleen, uterus, prostate, skeletal muscle, PBLs, placenta, small intestine) on charge-modified nylon membranes (multiple tissue blots #7760-1 and #7766-1, Clontech, Palo Alto, Calif.) were also hybidized.

Nitrocellulose membranes for the total RNA samples were hybridized with randomly primed [gamma-$^{32}$P]dCTP-labeled probes synthesized from a 1 kb fragment of EcoRI-NotI of ALP. Hybridization was performed overnight at 42° C. in 4xSSPE, 2.5xDenhardt's solution, 50% formamide, 200 μg/mL denatured salmon sperm DNA, 100 μg/mL yeast tRNA (Boehringer Mannheim, Ind.), 0.2% SDS with 5x10$^6$ cpm/mL of [gamma-$^{32}$P]dCTP-labeled DNA probe on a Techne Hybridizer H-1. The blots were washed with 2xSSC, 0.10% SDS, at 65° C. for 20 min twice followed by 0.5xSSC in 0.1% SDS at 65° C. for 20 min. The blots were exposed to a phospho-imaging screen for 24 hours and scanned on a Molecular Dynamics Phosphoimager SF.

For Clontech nylon-membrane blots, hybridization was performed at 42° C. overnight in 5xSSC, 2% SDS, 10xDenhardt's solution, 50% formamide, 100 μg/mL denatured salmon sperm DNA with 1–2x10$^6$ cpm/mL of [gamma-$^{32}$P] dCTP-labeled DNA probe. The blots were washed at room temperature in 2xSSC/0.05% SDS for 30 min and followed by at 50° C. in 0.2xSSC/0.1% SDS for 30 min, and exposed for 48 hours on Kodak XAR-2 film.

For analysis of expression using reverse-transcriptase-PCR detection, total RNA was isolated from various cell lines or fresh frozen tissues by centrifugation through a cesium chloride cushion. 20 μg of total RNA was reverse transcribed with random hexamers and Moloney human leukemia virus reverse transcriptase (Super-ScriptII, GIBCO BRL, Gaithersburg, Md.). PCR was then used to amplify cDNA encoding ALP. Reverse transcriptase PCR (RT-PCR) reactions lacking only the reverse transcriptase were performed as controls. PCR products were electrophoresed on 3% agarose gels, visualized by ethidium bromide staining and photographed on a UV light box.

The intensity of the fragment specific to ALP were compared among different RNA samples. A rating of 4 represents large quantities of ALP transcript while a rating of 0 represents little or none of the transcript was detected. It should be noted that detection of proteins by RT-PCR indicates a relatively higher abundance than detection by Northern blot as the RT-PCR technique utilizes total RNA whereas Northern blot analysis is performed using an enriched RNA source (mRNA).

Results:

A single ALP mRNA transcript of approximately 5.0 kb was visualized by Northern analysis. This transcript was identified in most of the normal tissue samples tested. However, the Northern analysis results shown in the Table 1 illustrate that the relative abundance of ALP mRNA is quite divergent. In normal tissues, ALP was identified in highest quantities in pancreas, followed by heart, testis, and skeletal muscle. Lower levels of the ALP transcript were identified in placenta, thymus, lung, brain, liver, spleen, uterus, prostate and small intestine. None of the ALP transcript was detected in colon, kidney and peripheral blood leucocytes (PBLs). ALP expression was also detected in normal human adipocytes by RT-PCR methods.

In Northern blots of total RNA from human tumor cell lines, the ALP RNA transcript was most abundant in NCI-H226 (lung tumor), SK-OV-3 (ovarian tumor), and RPMI 8226 (leukemia) cell lines. The transcript was identified at lower amounts in SNB-19 (CNS tumor), SF-268 (CNS tumor), SN12C (kidney tumor), SK-MEL-2 (melanoma), UACC-62 (melanoma), and UACC-257 (melanoma) cell lines. The ALP transcript was not detected in the remaining of 44 human tumor cell lines. A summary of expression of ALP is shown in Table 1 below.

TABLE 1

| Cell type | Origin | ALP |
|---|---|---|
| Thymus | Normal tissue | 0.5* |
| Lung | Normal tissue | 0.5* |
| Colon | Normal tissue | 0* |
| Testis | Normal tissue | 2* |
| Brain | Normal tissue | 0.5* |
| Heart | Normal tissue | 2* |
| Liver | Normal tissue | 0.5* |
| Pancreas | Normal tissue | 3* |
| Kidney | Normal tissue | 0* |
| Spleen | Normal tissue | 0.5* |
| Uterus | Normal tissue | 0.5* |
| Prostate | Normal tissue | 0.5* |
| Skeletal muscle | Normal tissue | 2* |
| PBLs | Normal tissue | 0* |
| Placenta | Normal tissue | 1* |
| Small intestine | Normal tissue | 0.5* |
| NCI-H226 | Lung tumor | 4 |
| SK-OV-3 | Ovarian tumor | 3 |
| SNB-19 | CNS tumor | 2 |
| U251 | CNS tumor | 1 |
| SF-268 | CNS tumor | 2 |
| RPMI 8226 | Leukemia | 3 |
| HTC15 | Colon tumor | 1 |
| UO-31 | Colon tumor | 1 |
| SN12C | Kidney tumor | 2 |
| SK-MEL-2 | Melanoma | 2 |
| SK-MEL-28 | Melanoma | 1 |
| UACC-62 | Melanoma | 2 |
| UACC-257 | Melanoma | 2 |
| T47D | Breast tumor | 1 |

*mRNA Northern blot.

ALP exhibits increased expression in tumor cells compared to their normal tissue counterparts. This differential expression suggests a possible disregulation or involvement of ALP in development or maintenance of the transformed phenotype.

EXAMPLE 3

Recombinant Expression of ALP

The following example illustrates the contruction of vectors for expression of recombinant ALP and the creation of recombinant cell lines expressing ALP.

Contruction of Expression Vectors

Expression constructs were generated by PCR-assisted mutagenesis in which the entire coding regions of ALP was introduced into the mammalian expression vectors pcDNAIII (Invitrogen) for transient expression analysis. Additional ALP constructs were made by oligonucleotide based PCR mutagenesis to convert atypical residues in the PTP-related domain back to the amino acids more commonly present in other catalytically active PTPs. These changes include: His to Tyr at amino acid 861 (See SEQ ID NO:2); Ala to Gly at amino acid 902; Phe to trp at amino acid 941; Glu to Asp at amino acid 995; and Ser to Ala at amino acid 1032. Additional constructs containing paired mutations as above were generated for amino acid positions 941/1032 and 902/1032. These constructs were ligated into the pcDNAIII mammalian expression vector behind the CMV promoter.

The entire ALP open reading frame excluding the initiating methionines was generated by PCR and ligated into PGEX vector (Pharmacia Biotech, Upsala, Sweden) for bacterial production of GST-Lusion proteins for immunization of rabbits for antibody production. This vector contains the glutathione-S-transferase coding sequence followed by a polylinker for generating recombinant fusion proteins. The GST moiety comprises the N-terminal portion of the fusion protein. The various ALP mutants were also inseted into the PGEX vecotr for production of recombinant protein reagents.

Transient Expression in Mammalian Cells

The pcDNAIII expression plasmids (10 μg DNA/100 mm plate) containing the wild-type and mutant forms of the ALP gene were introduced into 293 cells with lipofectamine (Gibco BRL). After 72 hours, the cells were harvested in 0.5 mL solubilization buffer (20 mM HEPES pH7.35, 150 mM NaCl, 10% glycerol, 1% Triton X-100, 1.5 mM $MgCl_2$, 1 mM EGTA, 2 mM phenylmethylsulfonyl fluoride, 1 μg/mL aprotinin). Sample aliquots were resolved by SDS polyacrylamide gel electrophoresis (PAGE) on 15%acrylamide/0.5% bis-acrylamide gels and electrophoretically transferred to nitrocellulose. Non-specific binding was blocked by preincubating blots in Blotto (phosphate buffered saline containing 5% w/v non-fat dried milk and 0.2% v/v nonidet P-40 (Sigma)), and recombinant protein was detected using antisera specific to the amino-terminal 352 residues (see below). Recombinant ALP protein migrated approximately 180 kDa, consistent with the predicted molecular weight of the 1–274 amino acid protein.

Endogenous ALP was detected as a 200 kD protein in Western blots of lysates from a variety of tumor cell lines including human glioblastomas (U87MG, ATCC HTB 14; U118MG, ATCC HTB 15; U138MG, ATCC HTB 16; A172, ATCC CRL 1620; Hs683, ATCC HTB 138), rodent gliomas (C6, ATCC 107), rodent pituitary tumors (ATT20, ATCC CCL 89; GH3, ATCC CCL 82.1), human neuroblastomas (SKNMC, ATCC HTB 10; IMR 32, ATCC CCL 127), and rodent adrenal pheochromocytomas (PC12, ATCC CRL 1721). ALP protein could not be immunoprecipitated from the non-transformed cell line NIH 3T3 (ATCC CRL 1658).

It is unclear why native ALP protein appears to be larger (200 kDa) than recombinant ALP detected in transfected 293 cells (180 kDa). The difference could be the result of alternative RNA splicing, or a post-translational modification in the cell lines where it is endogenously expressed. Preliminary experiments indicate that ALP is phosphorylated on serine and threonine residues in transfected 293 cells. In addition, several tyrosine-phosphorylated proteins are associated with ALP since they are detected in Western blots using an anti-phosphotyrosine antibody following immunoprecipitation of endogenous ALP from human tumor cell lines such as IMR32 after treatments with the phosphatase inhibitor pervanadate.

Generation of Virus Producing Cell Lines pLXSN recombinant constructs containing the ALP gene are transfected into an amphotropic helper cell line PA317 using $CaCl_2$ mediated transfection. After selection on G418, the cells are plated on normal media without G418 (500 μg/mL). Supernatants from resistant cells are used to infect the ecotropic helper cell line GP+E86, and cells again selected on G418. Resistant cells are again taken off G418, and the supernatants harvested every 8–12 hours and pooled as virus stock. Redemann et al., 1992, *Mol. Cell. Biol.* 12: 491–498. Viral stock titers are typically ~$10^6$/mL.

Stable Expression in Mammalian Cells

NIH-3T3, BALB/3T3 or other suitable cells are grown in 100 mm plates with DMEM (Gibco) containing 10% fetal calf serum (FCS). The cells are superinfected with the ALP retrovirus by adding approximately 3 mL viral supernatant to 15 mL culture media for approximately 24 hours. Cells expressing the retroviral constructs are then selected by growth in DMEM/10% FCS supplemented with 500 μg/mL G418.

EXAMPLE 4

Generation of Anti-ALP Antibodies

ALP-specific immunoreagents were generated by immunizing rabbits with the bacterially expressed N-terminal 352 amino acid portion of ALP expressed as a GST-fusion protein. Fusion protein was affinity purified using glutathione-sepharose colums (Pharmacia). Polyclonal antiserum against the N-terminal portion of ALP was generated by repeatedly immunizing rabbits with the purified GST-futions protein. Affinity-purified ALP antibody was obtained by binding serum IgG to ALP-GST-fusion protein immobilized on glutathione-sepharose and eluting with low pH and high salt.

EXAMPLE 5

Assay for ALP Activity Assay for Modulators of Catalytic Activity Materials and Methods Recombinant wild-type and mutant ALP proteins are purified from bacteria as GST-fusion proteins. Lysates are bound to a glutathione-sepharose matrix and eluted with glutathione. The purified proteins are then washed with 2×1 mL HNTG, followed by one wash with 1 mL of a buffer containing 100 mM 2-(N-morpholino)ethansulfonic acid (MES), pH 6.8, 150 mM NaCl, and 1 mM EDTA. The assay for phosphatase activity is essentially done as described by Pei et al.(1993) using p-nitrophenolphosphate (PNPP) as a generic PTP substrate. Briefly, after the last washing step, reactions are started by adding 50 mL Assay Buffer (100 mM MES pH 6.8, 150 mM NaCl, 10 mM DTT, 2 mM EDTA, and 50 mM p-nitrophenylphosphate) to the precipitates. Samples are incubated for 20 min. at 23° C. The reactions are terminated by mixing 40 μL of each sample (without beads) with 960 μL 1 N NaOH, and the absorbance of p-nitrophenol was determined at 450 nm. To control for the presence of ALP in the precipitates, the precipitates are boiled in SDS sample buffer and analyzed by SDS-PAGE. The presence of ALP is then detected by immunoblot analysis with anti-ALP antibodies.

EXAMPLE 6

Screening Systems for the Identification of Inhibitors of ALP Activity

Assays may be performed in vitro or in vivo and are described in detail herein or can be obtained by modifying existing assays, such as the growth assay described in patent application Ser. No. 08/487,088 (Lyon & Lyon Docket No. 212/276), filed Jun. 7, 1995, by Tang et al., and entitled "Novel Pharmaceutical Compounds," or the assays described in patent application Ser. No. 60/005,167 (Lyon & Lyon Docket No. 215/256), filed Oct. 13, 1995 by Seedorf et al., and entitled "Diagnosis and Treatment of TKA-1 related disorders," all of which are hereby incorporated herein by reference in their entirety including any drawings. Another assay which could be modified to use the genes of the present invention is described in International Application No. WO 94/23039, published Oct. 13, 1994, hereby incorporated herein by reference in its entirety including any drawings. Other possibilities include detecting kinase activity in an autophosphorylation assay or testing for kinase activity on standard substrates such as histones, myelin basic protein, gamma tubulin, or centrosomal proteins. Binding partners may be identified by putting the N-terminal portion of the protein into a two-hybrid screen or detecting phosphotyrosine of a dual specificity kinase (Fields and Song, U.S. Pat. No. 5,283,173, issued Feb. 1, 1994, incorporated by reference herein, including any drawings).

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

In view of the degeneracy of the genetic code, other combinations of nucleic acids also encode the claimed peptides and proteins of the invention. For example, all four nucleic acid sequences GCT, GCC, GCA, and GCG encode the amino acide alanine. Therefore, if for an amino acid there exists an average of three codons, a polypeptide of 100 amino acids in length will, on average, be encoded by $3^{100}$, or $5 \times 10^{47}$, nucleic acid sequences. Thus, a nucleic acid sequence can be modified to form a second nucleic acid sequence, encoding the same polypeptide as endoded by the first nucleic acid sequences, using routine procedures and without undue experimentation. Thus, all possible nucleic acids that encode the claimed peptides and proteins are also fully described herein, as if all were written out in full taking into account the codon usage, especially that preferred in humans. Furthermore, changes in the amino acid sequences of polypeptides, or in the corresponding nucleic acid sequence encoding such polypeptide, may be designed or selected to take place in an area of the sequence where the significant activity of the polypeptide remains unchanged. For example, an amino acid change may take place within a β-turn, away from the active site of the polypeptide. Also changes such as deletions (e.g. removal of a segment of the polypeptide, or in the corresponding nucleic acid sequence encoding such polypeptide, which does not affect the active site) and additions (e.g., addition of more amino acids to the polypeptide sequence without affecting the function of the active site, such as the formation of GST-fusion proteins, or additions in the corresponding nucleic acid sequence encoding such polypeptide without affecting the function of the active site) are also within the scope of the present invention. Such changes to the polypeptides can be performed by those with ordinary skill in the art using routine procedures and without undue experimentation. Thus, all possible nucleic and/or amino acid sequences that can readily be determined not to affect a significant activity of the peptide or protein of the invention are also fully described herein.

Other embodiments are within the following claims.

What is claimed is:

1. An isolated, enriched or purified nucleic acid molecule comprising a nucleotide sequence that
   (a) encodes a polypeptide having the full length amino acid sequence set forth in SEQ ID NO:2; or
   (b) is the full complement of the nucleotide sequence of (a).

2. The nucleic acid molecule of claim 1, wherein said nucleic acid molecule is isolated, enriched, or purified from a mammal.

3. The nucleic acid molecule of claim 2, wherein said mammal is a human.

4. The isolated, enriched or purified nucleic acid according to claim 1, wherein the nucleic acid molecule has the nucleotide sequence set forth SEQ ID NO: 1 or the full complement thereof.

5. An isolated, enriched or purified nucleic acid molecule comprising a nucleotide sequence which
   (a) encodes a polypeptide having the amino acid sequence set forth in amino acid residues 858–1096 of SEQ ID NO:2; or
   (b) is the full complement of the nucleotide sequence of (a).

6. The nucleic acid molecule according to claim 1, claim 4 or claim 5, further comprising a vector or promoter operably linked to the nucleotide sequence, so that the nucleic acid molecule is capable of expression in a host cell.

7. The nucleic acid molecule according to claim 1, claim 4 or claim 5, further comprising a second nucleic acid molecule,
   wherein said second nucleic acid molecule is fused to said nucleic acid molecule producing a fusion nucleic acid molecule, so that said fusion nucleic acid molecule encodes a fusion polypeptide.

8. A recombinant cell or recombinant tissue comprising a nucleic acid molecule according to claim 1, claim 4 or claim 5, and a host cell or host tissue, wherein said nucleic acid molecule is extragenomic or intragenomic.

9. The recombinant cell or recombinant tissue according to claim 8, further comprising a second nucleic acid molecule,
   wherein said second nucleic acid molecule is fused to said nucleic acid molecule producing a fusion nucleic acid molecule,
   so that said fusion nucleic acid molecule encodes a fusion polypeptide.

* * * * *